United States Patent [19]

Takeuchi et al.

[11] Patent Number: 5,719,130
[45] Date of Patent: Feb. 17, 1998

[54] ANTHRACYCLINE DERIVATIVE HAVING A TRIFLUOROMETHYLATED SUGAR

[75] Inventors: Tomio Takeuchi; Sumio Umezawa, both of Tokyo; Tsutomu Tsuchiya; Yasushi Takagi, both of Yokohama, all of Japan

[73] Assignee: Zaidan Hojin Biseibutsu Kagaku Kenkyu Kai, Tokyo, Japan

[21] Appl. No.: 714,050

[22] PCT Filed: Mar. 10, 1995

[86] PCT No.: PCT/JP95/00407

§ 371 Date: Sep. 9, 1996

§ 102(e) Date: Sep. 9, 1996

[87] PCT Pub. No.: WO95/24412

PCT Pub. Date: Sep. 14, 1995

[30] Foreign Application Priority Data

Mar. 11, 1994 [JP] Japan .................. 6-067714

[51] Int. Cl.$^6$ .................. C07H 15/252; A61K 31/70
[52] U.S. Cl. .................. 514/34; 536/6.4; 536/18.4; 552/201; 514/460; 514/25; 549/417
[58] Field of Search .................. 549/417; 552/201; 514/460, 34; 536/6.4

[56] References Cited

U.S. PATENT DOCUMENTS 5,374,746  12/1994  Ok et al. .................. 549/417

*Primary Examiner*—Johann Richter
*Assistant Examiner*—Laura L. Stockton
*Attorney, Agent, or Firm*—Larson & Taylor

[57] ABSTRACT

Novel anthracycline derivatives have now been produced, which exhibit higher antitumor activities and lower toxicities than those of daunomycin, adriamycin etc. that have been clinically used as anticancer agents. That is, a daunomycinone or adriamycinone derivative represented by the general formula (I):

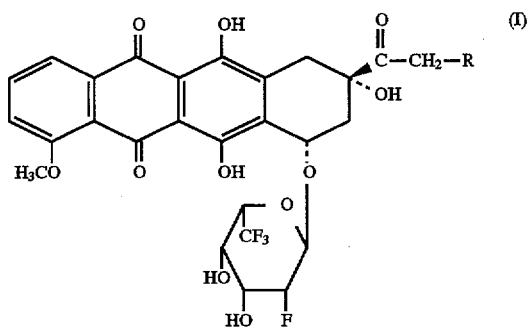

wherein R is a hydrogen atom or a hydroxyl group.

10 Claims, No Drawings

ANTHRACYCLINE DERIVATIVE HAVING A TRIFLUOROMETHYLATED SUGAR

This application is a 371 of PCT/JP95/00407 filed Mar. 10, 1995.

TECHNICAL FIELD

This invention relates to new anthracycline derivatives having a trifluoromethylated sugar which exhibit excellent anticancer or antitumor activities even at low dosages thereof and which are of low toxicity. This invention also relates to a pharmaceutical composition which comprises the new anthracycline derivative as an active ingredient. More particularly, this invention relates to such new anthracycline derivatives which exhibit anticancer or antitumor activities and are of low toxicity and which embrace 7-O-(2,6-dideoxy-2,6,6,6-tetrafluoro-α-L-talopyranosyl) daunomycinone or -adriamycinone as well as 7-O-(2,6-dideoxy-6,6,6-trifluoro-α-L-lyxo-hexopyranosyl) adriamycinone. Furthermore, this invention relates to new intermediate compounds which are useful for the synthesis of the above-mentioned new anthracycline derivatives.

BACKGROUND ART OF THE INVENTION

As the antibiotics of the anthracycline type are known daunomycin which is referred to as daunorubicin in the specification of U.S. Pat. No. 3,616,242, and adriamycin which is referred to as doxorubicin in the specification of U.S. Pat. No. 3,590,028. These compounds, namely daunomycin and adriamycin have broad anticancer activities against experimental tumors and have found wide-spread clinical utilities as chemotherapeutic antitumor agents.

Thus, daunomycin and adriamycin can exhibit somewhat strong anticancer or antitumor activities against various kinds of cancers or tumors but are not necessarily satisfactory as the anticancer agent or antitumor agent. Namely, daunomycin and adriamycin have been used widely as the chemotherapeutic antitumor agents for clinical treatments of tumor-bearing patients, but they are also known to bring about serious side-effects such as leukocytopenia, alopecia, myocardiopathy and others, in many instances.

Hitherto, it has hence been attempted to produce newly various kinds of daunomycin-related compounds for the purpose of providing such daunomycin-related compounds which have much enhanced anticancer or antitumor activities but have low toxicities. As some results of the attempts made hitherto, there have been proposed several compounds which are known, for example, as aclacinomycins A and B; 4'-O-tetrahydropyranyl-adriamycin; and N-mono-benzyl- or N-di-benzyl-adriamycin.

Besides, U.S. Pat. No. 4,427,664 specification discloses 7-O-(3,4-di-O-acetyl-2,6-dideoxy-2-iodo-α-L-mannohexopyranosyl)daunomycinone and 7-O-(3,4-di-O-acetyl-2,6-dideoxy-2-iodo-α-L-talo-hexopyranosyl)daunomycinone.

The present inventors had proceeded with investigations in an attempt to provide such derivatives of daunomycin or adriamycin which have better anticancer or antitumor activities and lower toxicities than daunomycin or adriamycin. As parts of the outcomes of the investigations, the present inventors already synthesized some of the daunomycin derivatives and the adriamycin derivatives in which the sugar moiety of daunomycin and adriamycin has been modified chemically. For instance, the present inventors already reported 4'-O-tetrahydropyranyl-daunomycin or -adriamycin as well as 3'-deamino-3'-morpholinodaunomycin or -adriamycin.

Furthermore, the present inventors succeeded in synthesizing such anthracycline derivatives having anticancer or antitumor activities and represented by the following general formula (A)

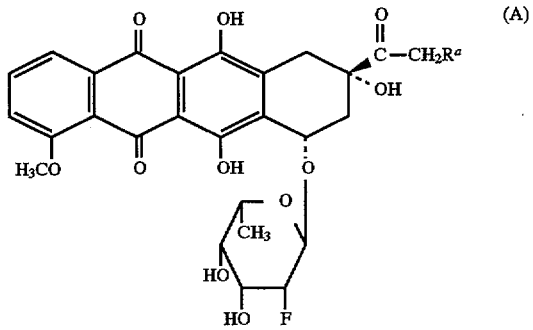

wherein $R^a$ means a hydrogen atom or a hydroxyl group, for example, 7-O-(2,6-dideoxy-2-fluoro-α-L-talopyranosyl) daunomycinone and 7-O-(2,6-dideoxy-2-fluoro-α-L-talopyranosyl)adriamycinone (Japanese Patent Application First Publication "Kokai" No. 145097/87 and European Patent No. 0230013).

The present inventors also succeeded in synthesizing such antitumor anthracycline derivatives represented by the general formula (B)

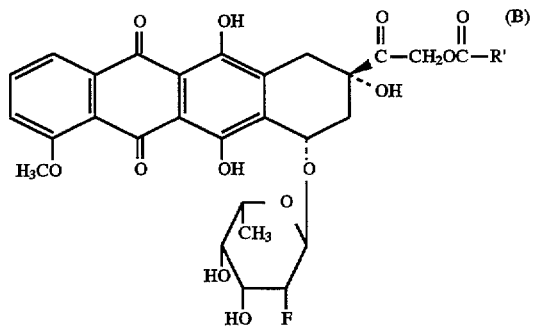

wherein R' means a group —$(CH_2)_m$H, where m is an integer of 1–6, or a group —$(CH_2)_n$—COOH, where n is zero or an integer of 1–10 (Japanese Patent Application First Publication "Kokai" No. 141992/88 and European Patent No. 0275431).

The present inventors further had conducted different investigations in an attempt to synthesize newly such novel anthracycline derivatives which exhibit higher anticancer or antitumor activities and lower toxicities than those of daunomycin, adriamycin and the antitumor compounds of the above-mentioned formulae (A) and (B).

The anticancer or antitumor activities of the antitumor compounds of the general formulae (A) and (B) mentioned above are remarkedly superior to those of daunomycin and adriamycin but are not yet satisfactory to a full extent. Accordingly, it is now still desirable to obtain such new anthracycline derivatives which can have much more enhanced anticancer or antitumor activities. In order that an anticancer or antitumor compound will be able to exhibit a high anticancer or antitumor activity, it is required that the anticancer or antitumor compound which has been administered should be capable of being readily uptaken by the cancer or tumor cells. It is also known that, in general, an anticancer or antitumor compound after the administration thereof will be distributed at different concentrations in the different organs of the living body. Thus, for use with a purpose of therapeutically treating different sorts of cancers and tumors which are formed in different local parts of the living body, it is demanded to synthesize and exploit a new anticancer or antitumor agent which possesses a property such that the resulting new antitumor anticancer or antitumor agent is capable of distributing into the different organs of the living body in a way different from the conventional anticancer or antitumor agent, that is to say, such property that the resulting new anticancer or antitumor agent is capable of exhibiting different behaviors of the transportation into organs from those of the conventional anticancer or antitumor agent.

DISCLOSURE OF THE INVENTION

In order to meet the demand as stated above, the present inventors have continued some researches with an object to synthesize a class of new anthracycline derivative containing a trifluoromethylated sugar as a moiety of the molecule.

As a result of the researches, the present inventors have now succeeded in synthesizing, as new compounds, 1-O-acetyl derivative of 2,6-dideoxy-2,6,6,6-tetrafluoro-α-L-talopyranose as well as a 2,6-dideoxy-2,6,6,6-tetrafluoro-α-L-talopyranosyl halide and its 3,4-di-O-protected derivatives through a multi-stages method which starts from methyl α-D-lyxopyranoside.

Further, the present inventors have now succeeded in synthesizing, as the new anthracycline derivatives containing the trifluoromethylated sugar, such novel daunomycinone or adriamycinone derivatives having a general formula (I) given hereinafter, by means of a process which comprises utilizing the newly synthesized derivatives of 2,6-dideoxy-2,6,6,6-tetrafluoro-α-L-talopyranose and condensing a 2,6-dideoxy-2,6,6,6-tetrafluoro-α-L-talopyranosyl group with the hydroxyl group at the 7-position of daunomycinone or adriamycinone. The present inventors also have found that even when an anthracycline derivative having the general formula (I) is administered at low dosages into test animals, the anthracycline derivative so administered can display a high anticancer or antitumor activity, and that any development of acute toxicity does not take place in the test animals having received the administration of the anthracycline derivative at the low dosages which can give high anticancer or antitumor effects in the test animals by the administration of said anthracycline derivative.

In a first aspect of this invention, therefore, there is provided a daunomycinone or adriamycinone derivative represented by the following general formula:

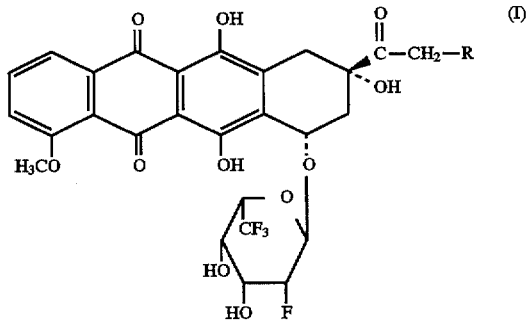

wherein R is a hydrogen atom or a hydroxyl group.

Examples of the daunomycinone or adriamycinone derivative of the general formula (I) include the under-mentioned compounds (a) and (b) according to this invention. (1) Compound (a): 7-O-(2,6-dideoxy-2,6,6,6-tetrafluoro-α-L-talopyranosyl)daunomycinone represented by the formula:

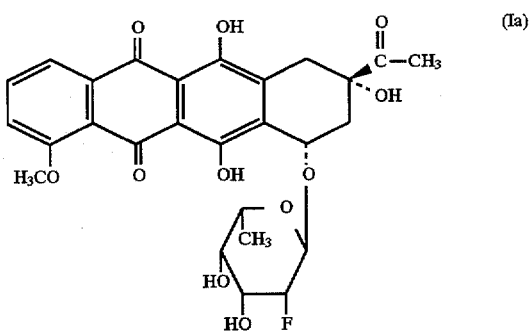

(see Example 1 given hereinafter). (2) Compound (b): 7-O-(2,6-dideoxy-2,6,6,6-tetrafluoro-α-L-talopyranosyl) adriamycinone represented by the formula:

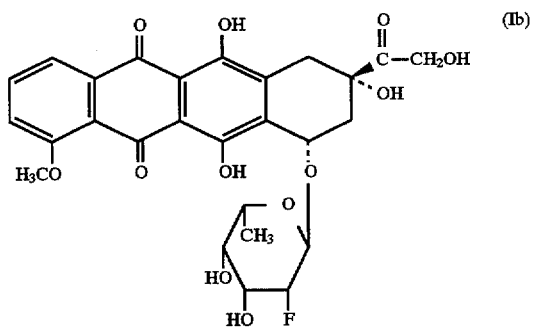

(see Example 2 given hereinafter).

The anthracycline derivatives of the formula (Ia) and formula (Ib) above are such compounds in which the trifluoromethyl group present at the 6-position of the sugar moiety of the anthracycline is a hydrophobic group and is also a strongly electron-withdrawing group. Thus, the anthracycline derivatives of the formulae (Ia) and (Ib) can be expected to show the under-mentioned properties in the living body owing to the presence of the trifluoromethyl group therein. Namely, 1) the compounds of the formula (Ia) and formula (Ib) have an enhanced lipophilicity for the whole molecule and thereby are capable of being uptaken much easily by the cancer or tumor cells. 2) The compounds of the formula (Ia) and formula (Ib) have the enhanced lipophilicity for the whole molecule so that the behaviors of transportation into organs of these compounds have been modified. Much more detailed, daunomycin and adriamycin can be converted into hydrophlic compounds by forming their acid addition salts. In contrast thereto, however, it appears that the compounds of the formula (Ia) and formula (Ib) have gained from their enhanced lipophilicity such characteristics that they can show behaviors of "in vivo" transportation different from those of the conventional anthracycline-type antibiotics. 3) The 6-trifluoromethyl group of the compounds of the formula (Ia) and formula (Ib) is the electron-withdrawing group and can stabilize the glycoside linkage between the sugar moiety and the aglycon of the anthracycline and also can lead to an enhanced anticancer or antitumor activity and a reduced toxicity of the present compounds.

Through some tests, it has been confirmed that the compounds of the general formula (I) according to this invention have markedly high antitumor activities against experimental tumors in animals, and that the antitumor activities of the compounds of this invention are comparable with or remarkably superior to the antitumor activities of daunomycin and adriamycin.

Some examples of tests are now described below to show the antitumor activities of the compound of the above Meanwhile, the symbol ">" shown in Table 1 indicates that such mice which could be cured by the administration of the test compound and survive for 60 days or longer were observed at a rate of at least one mouse among the four mice tested in a group.

TABLE 1

|  | % Increase in life-span (T/C, %) Dosage (mg/kg/day) | | | | | |
|---|---|---|---|---|---|---|
| Compound tested | 5 | 2.5 | 1.25 | 0.6 | 0.3 | 0.15 |
| 7-O-(2,6-Dideoxy-2,6,6,6-tetrafluoro-α-L-talopyranosyl) daunomycinone (Compound (a) of this invention) | 158* | 210* | 294 | 132 | 119 | 106 |
| 7-O-(2,6-Dideoxy-2,6,6,6-tetrafluoro-α-L-talopyranosyl) adriamycinone (Compound (b) of this invention) | 128* | 233* | >348 | >459 | >407 | 144 |
| 7-O-(2,6-Dideoxy-2-fluoro-α-L-talopyranosyl)- daunomycinone (FT-DM) (Comparative) | 184 | 217 | 171 | 125 | 105 | 105 |
| 7-O-(2,6-Dideoxy-2-fluoro-α-L-talopyranosyl)- adriamycinone (FT-ADM) (Comparative) | >740 | >352 | 275 | 185 | 182 | 127 |
| Daunomycin (as hydrochloride) (Comparative) | 138* | 171* | 158 | 145 | 112 | 132 |
| Adriamycin (as hydrochloride) (Comparative) | 177* | 273* | 330 | 208 | 132 | 140 |

Notes;
Asterisks (*) indicate that development of toxicity such as toxicity-related death or a body weight loss was observed on the corresponding mice tested.

formula (Ia) and the compound of the above formula (Ib) which are embraced by the compounds of the general formula (I) according to this invention.

TEST EXAMPLE 1

In this Example, some tests were made to demonstrate the antitumor activities of the compounds of this invention which were shown against leukemia in $CDF_1$ mice as induced by a mouse leukemia with Leukemia L-1210 cells.

Thus, to evaluate the antitumor effects of the new compounds of this invention against experimental tumors in animals, $CDF_1$ mice (four mice per group) were intraperitoneally transplanted with cells of Leukemia L-1210 at an amount of $1 \times 10^5$ cells/mouse. Since an elapsed time of 24 hours from the transplantation of the leukemia cells, a test compound according to this invention was administered intraperitoneally to the mice under test for 9 consecutive days once per day. The mice so treated were observed for 60 days after the administration of the test compound. While, mice of the control group (the untreated group) were administered with only physiological saline after the transplantation of the L-1210 cells. During the observation period, the numbers of the surviving mice in the treated group and in the control group were counted, and the mean survival days of mice in the treated group and in the control group were then calculated. From the mean survival day (C) of the untreated mice of the control group and the mean survival day (T) of the treated mice of the treated group, there were evaluated percentages (%) of the increase in the life-span of the treated mice, as T/C %. For a comparison purpose, 7-O-(2,6-dideoxy-2-fluoro-α-L-talopyranosyl)daunomycinone (abbreviation: FT-DM); 7-O-(2,6-dideoxy-2-fluoro-α-L-talopyranosyl)adriamycinone (abbreviation: FT-ADM); daunomycin and adriamycin were also tested in the same manner as above. The test results so obtained are shown in Table 1 below. Incidentally, the mean survival day of mice of the control group (the untreated group) was amounting to 8 to 9 days, and the mean survival day of mice of the comparative groups having received the administration of adriamycin was varying dependently on the dosage of adriamycin.

In the tests shown above, it is noticed that all the compounds of the general formula (I) according to the first aspect of this invention exhibit high antitumor activities. Thus, Compound (a) of this invention at a dosage of 1.25 mg/kg exhibited much higher therapeutic effects against the L-1210 leukemia than daunomycin, and said Compound (a) at low dosages of 0.6 to 1.25 mg/kg exhibited much higher therapeutic effects than FT-DM as the comparative drug. In particular, when Compound (b) of this invention was administered, this Compound (b) had remarkably excellent antitumor activities such that the mice as treated with the administration of Compound (b) at low dosages of 0.3 to 1.25 mg/kg had gained such increases (%) in the life-span (as T/C, %) which amounted to a range of from more than 348% to more than 459%, and that the mouse which could survive for 60 days (namely, the mouse as fully cured from the leukemia) can be observed. It can hence be seen that Compound (b) of this invention has extraordinarily higher anticancer or antitumor activities than those of adriamycin. Further, it can also be seen that Compound (b) of this invention has the enhanced anticancer or antitumor activities over the whole range of low dosages of from 0.15 to 1.25 mg/kg of Compound (b), as compared with the comparative drug, FT-ADM, and that this Compound (b) as administered particularly at dosages of 0.3 to 1.25 mg/kg has remarkably enhanced anticancer or antitumor activities.

On the other hand, the present inventors have now further attempted to synthesize such new anthracycline derivatives which are analogous in the chemical structure to the anthracycline derivative of the general formula (I) according to the first aspect of this invention but in which the fluoro group at the 2-position of the adriamycinone derivative of the above formula (Ib) is replaced by a hydrogen atom. The present inventors have thus continued researches for this attempt. As a result of these further researches, the presnet inventors have now succeeded in synthesizing, as new sugar compounds, 1-O-acetyl derivative of 2,6-dideoxy-6,6,6-trifluoro-α-L-lyxo-hexopyranose as well as 2,6-dideoxy-6,6,6-trifluoro-α-L-lyxo-hexopyranosyl bromide and 3,4-di-O-protected derivatives thereof through a multi-staged method which starts from a known compound, methyl 4-deoxy-β-L-erythro-pentopyranoside.

And, the present inventors have now succeeded in synthesizing, as another anthracycline derivatives containing a trifluoromethylated sugar, such novel adriamycinone derivatives having a general formula (II) given hereinafter, by means of a process which comprises utilizing the above-mentioned derivatives of 2,6-dideoxy-6,6,6-trifluoro-α-L-lyxo-hexopyranose and condensing a 2,6-dideoxy-6,6,6-trifluoro-α-L-lyxo-hexopyranosyl group with the hydroxyl group at the 7-position of adriamycinone. The present inventors also have found that even when an anthracycline derivative having the general formula (II) is administered at low dosages to test animals, the anthracycline derivative so administered can display a high anticancer or antitumor activity, and that development of acute toxicity does not take place in the test animals having received the administration of the anthracycline derivative of the formula (II) at the low dosages which can give high anticancer or antitumor effects in the test animals by the administration of said anthracycline derivative.

In a second aspect of this invention, therefore, there is provided 7-O-(2,6-dideoxy-6,6,6-trifluoro-α-L-lyxo-hexopyranosyl)adriamycinone which is an adriamycinone derivative represented by the following formula:

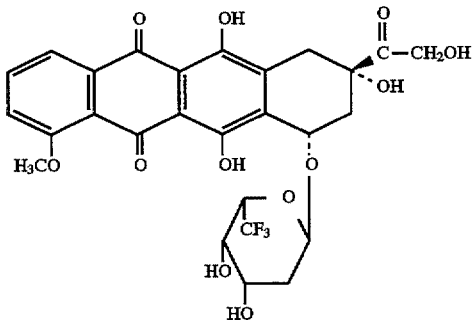

(II)

It has been found that the adriamycinone derivative of the formula (II) has a steric hinderance of its molecule which is less than that of the derivative of the formula (Ib) according to the first aspect of this invention.

Next, some examples of tests are described to show the antitumor activities of the adriamycinone derivative of the formula (II) which is referred to as Compound (c) in the following

TEST EXAMPLE 2

In this Example, some tests were made to demonstrate the antitumor activities of Compound (c) of this invention which were shown against leukemia in $CDF_1$ mice as induced by a mouse leukemia with Leukemia L-1210 cells. Thus, to evaluate the antitumor effects of Compound (c) of this invention against experimental tumors in animals, $CDF_1$ mice (four mice per group) were intraperitoneally transplanted with cells of Leukemia L-1210 at an amount of $1 \times 10^5$ cells/mouse. Since an elapsed time of 24 hours from the transplantation of the leukemia cells, Compound (c) of this invention was administered intraperitoneally to the mice under test for 9 consecutive days once per day. The mice so treated were observed for 30 days after the administration of the test compound. While, mice of the control group (the untreated group) were administered with only physiological saline after the transplantation of the L-1210 cells. During the observation period, the numbers of the surviving mice in the treated group and the control group were counted, and the mean survival days of mice in the treated group and in the control group were then calculated. From the mean survival day (C) of the untreated mice of the control group and the mean survival day (T) of the treated mice of the treated group, there were evaluated percentages (%) of the increase in the life-span of the treated mice as T/C %. For a comparison purpose, adriamycin was also tested in the same manner as above. The test results obtained are shown in Table 2 below. Incidentally, the mean survival day of mice of the control group (the untreated group) was amounting to 8 to 9 days, and the mean survival day of mice of the comparative groups having received the administration of adriamycin was varying dependently on the dosage of adriamycin.

Meanwhile, the symbol ">" shown in Table 2 indicates that such mice which could be cured by the administration of the test compound and survive for 30 days or longer were observed at a rate of at least one mouse among the four mice tested in a group.

TABLE 2

| | % Increase in life-span (T/C, %) Dosage (mg/kg/day) | | | | | |
|---|---|---|---|---|---|---|
| Compound tested | 5 | 2.5 | 1.25 | 0.6 | 0.3 | 0.15 |
| 7-O-(2,6-Dideoxy-6,6,6-trifluoro-α-L-lyxo-hexopyranosyl)adriamycinone (Compound (c) of this invention) | 135* | 194* | 203 | >283 (2/4) | >329 (3/4) | >335 (3/4) |
| Adriamycin (as hydrochloride) (Comparative) | 177* | 273* | 330 | 208 | 132 | 140 |

Notes;
Asterisks (*) indicate that development of toxicity such as toxicity-related death or a body weight loss was observed on the corresponding mice tested.

With Test Example 2 above, it is noticed that Compound (c) of this invention as given at low dosages of from 0.6 to 0.15 mg/kg had gained such percentages of the increase in the life-span (as T/C, %) which amounted to a range of from more than 283% to more than 335%, and that there were obtained such remarkable curative effects against the tumor that, amongst the totally 12 test mice treated with Compound (c) of this invention given at the low dosages of the above-mentioned range, 8 mice under test could survive for 30 days. Thus, it is observed that Compound (c) of this invention exhibits very much higher anticancer or antitumor activities than those of adriamycin.

By the way, the results of the tests of Compound (c) of this invention as shown in Table 2 of Test Example 2 are to show the observations which were obtained with the test mice for the test period of 30 days from the transplantation of L-1210 tumor cells into the mice. It can be presumed that if the observation period would be extended to 60 days from 30 days, the differences in the anticancer or anticancer activities between Compound (c) of this invention and adriamycin should become greater than those shown in Table 2.

Furthermore, in order to estimate the antitumor activities of Compound (a) and Compound (b) of this invention represented by the general formula (I), as well as the adriamycinone derivative represented by the formula (II) (namely, Compound (c) of this invention), some "in vitro" tests for inhibiting proliferation of cancer cells were conducted as shown below.

TEST EXAMPLE 3

The above-mentioned Compound (a), Compound (b) or Compound (c) according to this invention were added at varying concentrations to mouse leukemia, P388 cells or adriamycin-resistant P388 cells (P388/ADR) which had been incubated in test tubes containing an appropriate culture medium. The incubation of the tumor cells were then continued for 72 hours from the addition of the test compound, and determination was made to evaluate such concentrations of the test compound which could inhibit the growth of the leukemia cells by 50% (namely, $IC_{50}$, ng/ml). FT-DM, FT-ADM and adriamycin (as the hydrochloride) were used as comparative compounds and were tested in the same manner as above. The test results obtained are summarized in Table 3 below.

TABLE 3

| Test Compound | $IC_{50}$ (ng/ml) | |
| --- | --- | --- |
| | P388 | P388/ADR |
| Compound (a) of this invention | <9.8 | 28 |
| Compound (b) of this invention | <9.8 | 43 |
| Compound (c) of this invention | <9.8 | 170 |
| FT-DM (Comparative) | 33 | 150 |
| FT-ADM (Comparative) | 3.4 | 92.8 |
| Adriamycin (as hydrochloride) (Comparative) | 17 | 510 |

From the results of Table 3 above, it is found that both of Compounds (a) and (b) of this invention have higher antitumor activities against the above-mentioned tumor cells under test than adriamycin and especially can inhibit the growth of P388/ADR cell at the remarkedly lower concentrations than adriamycin. It is also found that both of Compounds (a) and (b) of this invention can inhibit the growth of the P388/ADR cell at the substantially same concentrations as or at the lower concentrations than FT-DM and FT-ADM in term of $IC_{50}$ and can have the antitumor activities to the same degree as or to a higher degree than those of FT-DM and FT-ADM. Further, when compared with FT-ADM, Compound (b) of this invention as tested in the "in vitro" tests is found to have the antitumor activities against the P388 cell to a substantially same degree as that of FT-ADM, so that Compound (b) is not found to be greatly different from FT-ADM in respect of their antitumor activities. While, as shown in Table 1 hereinbefore, Compound (b) of this invention as tested in the "in vivo" tests can exhibit the remarkedly higher antitumor effects in mice than FT-ADM even when Compound (b) was administered to mice at the low dosages. This can be deemed to suggest that the above Compounds (a) and (b) of this invention exhibit are not greatly different from FT-ADM in respect of the antitumor activities which are tested in the "in vitro" tests, but in spite of this, Compounds (a) and (b) of this invention are able to much more readily reach the cancer or tumor cells in vivo owing to the presence of the trifluoromethyl group at the 6-position of the sugar moiety of the aforesaid compounds of this invention and therefore can exhibit the enhanced anticancer or antitumor effects in vivo, as compared with FT-ADM.

Also from the results of Table 3, it is found that Compound (c) of this invention has the higher antitumor activities than adriamycin and can inhibit the growth of P388/ADR cell at such concentrations thereof which are ⅓-folds lower than that of adriamycin in terms of their $IC_{50}$.

Besides, Compound (c) according to the second aspect of this invention exhibits the antitumor activity against P388 cell to a substantially same degree as that of Compound (b) according to the first aspect of this invention. This will indicate that the replacement of the fluoro group by a hydrogen atom at the 2-position of the Compound (b) of this invention does not deteriorate the antitumor activity of Compound (c) of this invention.

Daunomycin or adriamycin employed as the comparative drug in Test Examples 1–3 above is a carcinostatic agent which is actually used in clinical treatments. Daunomycin or adriamycin is administered to men at doses in a range of from 0.4 mg/kg to 2 mg/kg depending on the types of cancers to be treated. When the clinically utilized daunomycin or adriamycin is administered at a dose of from 2.5 mg/kg/day to 5 mg/kg/day to the mice which has been inoculated with the L-1210 cells, daunomycin and adriamycin each exhibit the anticancer or antitumor effects such that the percentages (%) of increase in life-span (T/C, %) so obtained amounts to about 138% to 171% and to approximately 330% at maximum, with being accompanied by development of toxicity.

In contrast, it should be worthy to note that Compounds (b) and (c) of this invention as administered at an appropriate low dosage in a range of from 0.3 mg/kg/day to 1.25 mg/kg/day are not accompanied by development of toxicity but are able to afford the remarkably higher percentages of increase in the life-span (as T/C, %) than daunomycin and adriamycin, and that Compounds (b) and (c) of this invention so administered can exhibit very much excellent antitumor effects such that the percentages of increase in the life-span obtained are amounting to about 300% or more, with involving some cases of the complete curing of the L-1210 cell-inoculated mice. Therefore, among Compounds (a), (b) and (c) of this invention, particularly Compounds (b) and (c) of this invention have such an advantage that their antitumor effects can be expected to be obtained in the clinical treatments of cancer-bearing patients even when Compounds (b) and (c) are administered at a non-large dosage to the patients.

From the foregoing, it is considered that the novel anthracycline derivatives having the general formula (I) and the formula (II) respectively according to the first aspect and the second aspect of this invention have excellent antitumor activities and have low toxicities. Thus, said novel anthracycline derivatives are very much useful as the antitumor drug which is practically usable in the clinical treatments of the patients, and they are expectable to be valuable for use in therapeutic treatments of various kinds of tumors similarly to daunomycin or adriamycin. Consequently, the compounds of the general formula (I) according to the first aspect of this invention as well as the compound of the formula (II) according to the second aspect of this invention can be utilized usefully as therapeutic agents for tumors or cancers in the medicinal treatments of solid cancers, ascitic cancers and the like.

According to a third aspect of this invention, therefore, there is provided an antitumor composition, characterized in that the composition comprises as an active ingredient a daunomycinone or adriamycinone derivative represented by the general formula (I) described hereinbefore, or an adriamycinone derivative represented by the formula (II) described hereinbefore, in combination with a pharmaceutically acceptable carrier.

When the compound of the general formula (I) or the formula (II) according to this invention is administered in practice, it may usually be administered by a parenteral route. It is also feasible to administer the compound of this invention orally after the compound is mixed with a pharmaceutically acceptable solid or liquid carrier which is conventionally used in the pharmaceutic field, followed by formulating the resultant mixture into various preparation forms such as powder, granules, tablets or syrups, or injectable solutions and suspensions.

For a usual method for the administration, the compound of this invention may be administered to animals in the form of an injectable solution or suspension of the compound by intraperitoneal injection, subcutaneous injection, blood vessel injection, either intravenous or intra-arterial, or local injection and the like. The compound of this invention may be administered to humans also in the form of an injectable solution or suspension of the compound by blood vessel injection, either intravenous or intra-arterial, or local injection and the like. The compound of this invention may be administered continuously or intermittently at such dosages and to such an extent that the total dosage would not exceed a certain level as determined in view of results of animal tests and various circumstances. The administration of the compound of this invention should, of course, be effected by changing the dosages of the compound appropriately in accordance with the way of administration and the conditions of the patients or animals to be treated, such as age, body weight, sex, sensitivity, foods, administration time, administration route, drugs to be administered in combination and the seriousness of patients or disease, etc. The compound of this invention may be administered at a substantially same dose as that of daunomycin or adriamycin when the compound is used as an antitumor or anticancer agent. Optimum dosage and frequency of administration of the compound of this invention under certain specific conditions must be determined by medicinal experts through preliminary tests in view of the above-mentioned guideline. These requirements for administration are equally applied to the oral administration of the compound of this invention.

BEST EMBODIMENTS FOR THE INVENTION

Next, processes for the preparation of the daunomycinone derivative or adriamycinone derivative of the general formula (I) according to the first aspect of this invention are described below.

For the preparation of 7-O-(2,6-dideoxy-2,6,6,6-tetrafluoro-α-L-talopyranosyl)daunomycinone represented by the general formula (I) or the formula (Ia), it is necessary to use 1-O-acetyl derivative of 2,6-dideoxy-2,6,6,6-tetrafluoro-α-L-talopyranose or 3,4-di-O-protected derivatives thereof, or a 3,4-di-O-protected-2,6-dideoxy-2,6,6,6-tetrafluoro-α-L-talopyranosyl iodide or bromide which are the new sugar compounds. The respective steps (1) to (13) involved in the method for the synthesis of these new sugar compounds are firstly explained below in brief. Referential Example 1 given hereinafter will be referred to as detailed descriptions of the reactions which are effected in the respective steps of said synthetic method.

In the following descriptions, abbreviations Bn and Ac appear in different formulae given hereinafter, wherein Bn means benzyl group and Ac means acetyl group.

Step (1):

A known compound, methyl α-D-lyxopyranoside [Compound (1)] of the formula

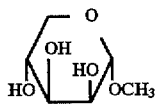

is reacted with diethylaminosulfur trifluoride [(C$_2$H$_5$)$_2$NSF$_3$] to fluorinate selectively only the 4-hydroxyl group of Compound (1), whereby there is produced methyl 4-deoxy-4-fluoro-α-L-ribopyranoside [Compound (2)] of the formula

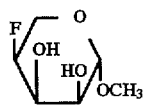

as a 4-deoxy-4-fluoro derivative of Compound (1), with accompanying reversion of the steric configuration of the starting compound.

Step (2):

The hydroxyl groups at the 2- and 3-positions of Compound (2) are benzylated by reaction with benzyl bromide, whereby there is produced methyl 2,3-di-O-benzyl-4-deoxy-4-fluoro-β-L-ribopyranoside [Compound (3)] of the formula

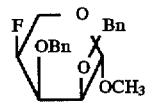

Step (3):

Compound (3) is hydrolyzed with acid to cleave the glycoside linkage at the 1-position of said compound, whereby there is produced 2,3-di-O-benzyl-4-deoxy-4-fluoro-L-ribopyranose [Compound (4)] of the formula

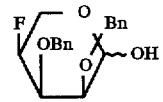

Step (4):

Compound (4) is reacted with 1,3-propanedithiol in the presence of boron trifluoride-ethyl ether to cleave the sugar ring of Compound (4), whereby there is produced 2,3-di-O-benzyl-4-deoxy-4-fluoro-L-ribose trimethylene dithioacetal [Compound (5)] of the formula

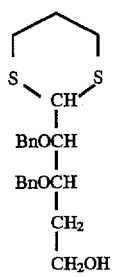

as a straight-chain compound of the dithioacetal type.

Step (5):

The primary hydroxyl group of Compound (5) is acetylated with acetic anhydride to produce 5-O-acetyl-2,3-di-O-benzyl-4-deoxy-4-fluoro-L-ribose trimethylene dithioacetal [Compound (6)] of the formula

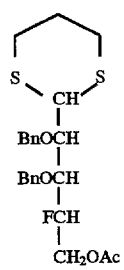

Step (6):

Compound (6) is reacted with mercury perchlorate in aqueous tetrahydrofuran in the presence of calcium carbonate to cleave the dithioacetal ring of Compound (6), whereby there is produced 5-O-acetyl-2,3-di-O-benzyl-4-deoxy-4-fluoro-aldehyde-L-ribose [Compound (7)] of the formula

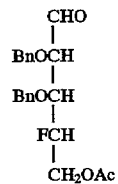

as an aldehyde-type compound.

Step (7):

Compound (7) is then reacted with trifluoromethyl-trimethylsilane in anhydrous tetrahydrofuran in the presence of tetrabutylammonium fluoride. Thereby, there are produced 6-O-acetyl-3,4-di-O-benzyl-1,5-dideoxy-1,1,1,5-tetrafluoro-L-altritol [Compound (8)] of the formula

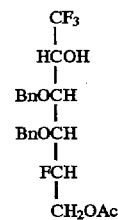

as an L-altritol derivative having a trifluoromethyl group incorporated therein and its 2-epimer [Compound (9)] of the formula.

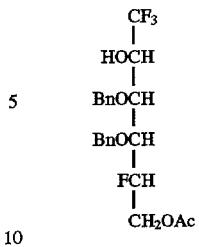

Step (8):

Compound (8) is treated with a methanolic solution of sodium methoxide to remove the acetyl group from Compound (8). There is thus produced 3,4-di-O-benzyl-1,5-dideoxy1,1,1,5-tetrafluoro-L-altritol [Compound (10)] of the formula

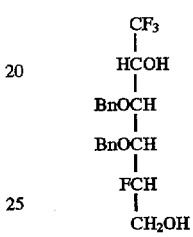

as a diol.

Step (9):

Reactions of oxidizing selectively the primary hydroxyl group of Compound (10) and forming simultaneously the ring of a pyranose are then conducted. For this purpose, the 2- and 6-hydroxyl groups of Compound (10) are trimethylsilylated, followed by effecting Collin's oxidation of the resulting trimethylsilylated product. Thus, the primary trimethylsilyloxy group of the resulting trimethylsilylated product is subjected to selective oxidation to afford an aldehyde product. This aldehyde product is then hydrolyzed with acid to remove the remaining trimethylsilyl group and concurrently bring about the cyclization reaction, whereby there is produced 3,4-di-O-benzyl-2,6-dideoxy-2,6,6,6-tetrafluoro-α-L-talopyranose [Compound (11)] of the formula

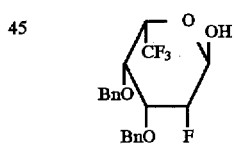

as a 2,6-dideoxy-2,6,6,6-tetrafluorotalopyranose derivative.

Step (10):

The 1-hydroxyl group of Compound (11) is then acetylated with acetic anhydride to produce 1-O-acetyl-3,4-di-O-benzyl-2,6-dideoxy-2,6,6,6-tetrafluoro-α-L-talopyranose [Compound (12)] of the formula.

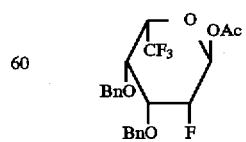

Step (11):

The benzyl groups at the 3- and 4-positions of Compound (12) are removed therefrom by catalytic reduction to produce 1-O-acetyl-2,6-dideoxy-2,6,6,6-tetrafluoro-α-L-talopyranose [Compound (13)] of the formula

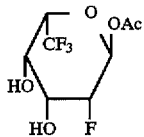

Step (12):
The hydroxyl groups at the 3- and 4-positions of Compound (13) are acetylated with acetic anhydride, whereby there is produced 1,3,4-tri-O-acetyl-2,6-dideoxy-2,6,6,6-tetrafluoro-α-L-talopyranose Compound (14)] of the formula

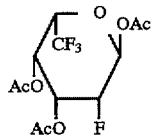

as a tri-O-acetylated product.

Step (13):
Compound (14) is reacted with iodotrimethylsilane [(CH$_3$)$_3$SiI] in anhydrous toluene, whereby there is produced 3,4-di-O-acetyl-2,6-dideoxy-2,6,6,6-tetrafluoro-L-talopyranosyl iodide [Compound (15)] of the formula

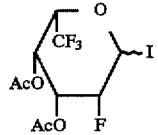

as a 1-iodo sugar.

The above Compound (11), Compound (12), Compound (13) and Compound (14) are new compounds. When Compound (11) or Compound (12) is reduced with hydrogen in the presence of a palladium catalyst in a conventional manner, it is feasible to remove the 3- and 4-benzyl groups of these compounds therefrom, whereby there can be produced 2,6-dideoxy-2,6,6,6-tetrafluoro-α-L-talopyranose or 1-O-acetyl-2,6-dideoxy-2,6,6,6-tetrafluoro-a-L-talopyranose. After the removal of the benzyl groups, it is also possible to introduce another optionally appropriate hydroxyl-protecting groups into the debenzylated product with aid of such methods for protecting hydroxyl group which are known in the chemistry of sugar.

According to a fourth aspect of this invention, therefore, there is provided, as new compound, a 3,4-di-O-protected- or unprotected-2,6-dideoxy-2,6,6,6-tetrafluoro-α-L-talopyranose or 1-O-acetyl derivative thereof, which is represented by the following general formula:

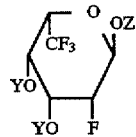

(III)

wherein the two Y are simultaneously hydrogen atoms or are simultaneously benzyl groups or acetyl groups as a hydroxyl-protecting group and Z is a hydrogen atom or an acetyl group.

As described in the above, Compound (15) is produced from Compound (14) by the iodination, and similarly from Compound (12) may be produced a corresponding 1-iodo sugar by reaction with an appropriate iodination agent. In place of the benzyl groups which protect the 3- and 4-hydroxyl groups of Compound (12) and Compound (14), another appropriate hydroxyl-protecting groups, for example, benzoyl group, may have been introduced thereinto. It is also possible to use an appropriate method of bromination in place of the iodination, so that a corresponding 1-bromo sugar can be synthesized.

According to a fifth aspect of this invention, therefore, there is provided, as new compounds, a 3,4-di-O-protected-2,6-dideoxy-2,6,6,6-tetrafluoro-L-talopyranosyl halide represented by the following general formula:

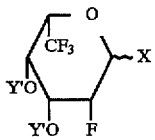

(IV)

wherein the two Y' are simultaneously acetyl groups or benzoyl groups as a hydroxyl-protecting group and X is an iodine or bromine atom.

Further, the aforesaid altritol Compound (10) is a new compound. When Compound (10) is reduced with hydrogen in the presence of a palladium catalyst under mild reaction conditions, the benzyl groups can be removed from Compound (10) to produce 1,5-dideoxy-1,1,1,5-tetrafluoro-L-altritol.

According to a sixth aspect of this invention, therefore, there is provided, as useful new intermediate compounds, 1,5-dideoxy-1,1,1,5-tetrafluoro-L-altritol or 3,4-di-O-benzyl derivative thereof, which is represented by the following general formula:

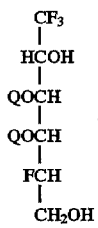

(V)

wherein Q is a hydrogen atom or a benzyl group.

(B) The production of 7-O-(2,6-dideoxy-2,6,6,6-tetrafluoro-α-L-talopyranosyl)daunomycinone of the formula (Ia) according to the first aspect of this invention, namely Compound (a) of this invention, may be conducted by a process which comprises condensing the aforesaid iodide Compound (15) or generally a 3,4-di-O-protected-2,6-dideoxy-2,6,6,6-tetrafluoro-α-L-talopyranosyl iodide or bromide of the general formula (IV) shown hereinbefore with the 7-hydroxyl group of daunomycinone, and then eliminating the remaining hydroxyl-protecting groups from the resultant condensation product by a conventional method. In this process, it is convenient that Compound (15) and daunomycinone are dissolved in dichloroethane and then condensed with each other in the presence of mercuric iodide, yellow-colored mercuric oxide and Molecular Seive 3A, followed by recovering the condensation product so obtained from the reaction solution and eliminating the protective acetyl groups from said α-L-condensation product by alkaline hydrolysis so that the target Compound (a) of this invention is produced (see Example 1 given hereinafter).

More generally, according to a seventh aspect of this invention, there is further provided a process for the preparation of 7-O-(2,6-dideoxy-2,6,6,6-tetrafluoro-α-L-talopyranosyl)daunomycinone of the formula (Ia) above, which comprises condensing the 7-hydroxyl group of daunomycinone with a 3,4-di-O-protected-2,6-dideoxy-2,6,6,6-tetrafluoro-α-L-talopyranosyl halide to produce a protected 7-O-(2,6-dideoxy-2,6,6,6-tetrafluoro-α-L-talopyranosyl)daunomycinone derivative represented by the formula:

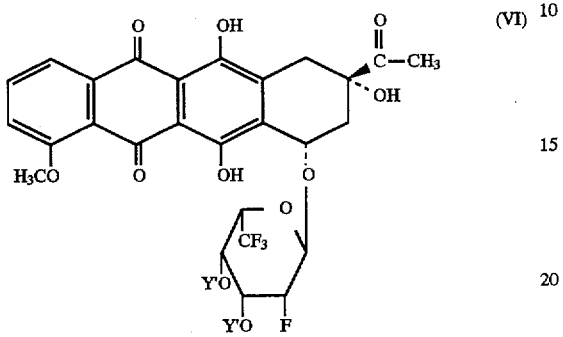

wherein Y' each is a hydroxyl-protecting group, and then eliminating the remaining hydroxyl-protecting group (Y') from the daunomycinone derivative of the formula (VI).

(C) The production of 7-O-(2,6-dideoxy-2,6,6,6-tetrafluoro-α-L-talopyranosyl)adriamycinone of the formula (Ib) according to the first aspect of this invention, namely Compound (b) of this invention, may be conducted by a process which comprises converting the methyl group at the 14-position of the daunomycinone compound of the formula (Ia) shown above into a hydroxymethyl group (see Japanese patent application pre-publication No. 299296/89 or U.S. Pat. No. 4,125,607).

For a process of producing the aforesaid Compound (b) of this invention, therefore, there is provided according to an eighth aspect of this invention a process for the preparation of 7-O-(2,6-dideoxy-2,6,6,6-tetrafluoro-α-L-talopyranosyl) adriamycinone of the formula (Ib), characterized in that the process comprises subjecting the carbonyl group at the 13-position of 7-O-(2,6-dideoxy-2,6,6,6-tetrafluoro-α-L-talopyranosyl)daunomycine of the formula (Ia) above to a dimethylketalation reaction by reacting with methyl orthoformate, thereby to produce a compound having the formula:

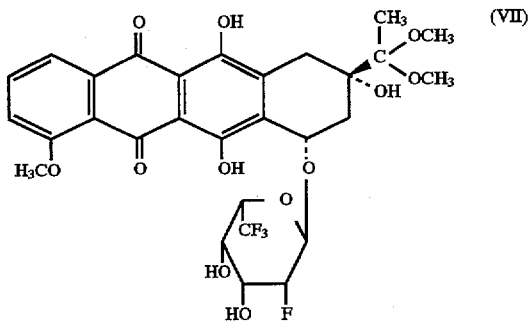

and then reacting the compound of the formula (VII) with bromine to produce a compound having the formula:

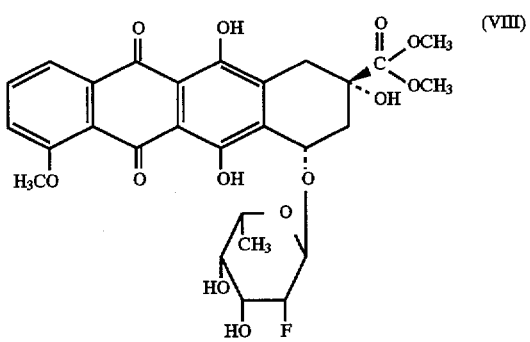

and eliminating the dimethylketal group from the compound of the formula (VIII), either by hydrolyzing the compound (VIII) with hydrobromic acid or by subjecting the compound (VIII) to a ketal conversion with acetone, to produce a compound having the formula:

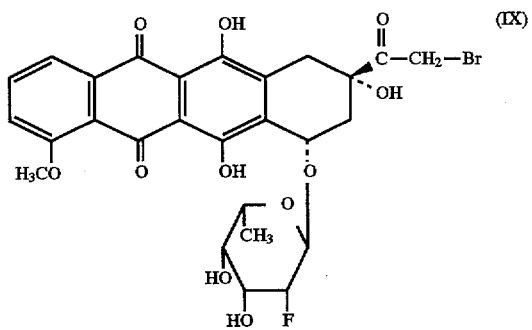

and subsequently hydrolyzing the compound of the formula (IX) to produce the compound of the formula (Ib).

In the above-mentioned process for the production of the compound of the formula (Ib), the dimethylketalation reaction of the 13-carbonyl group of the daunomycinone derivative of the formula (Ia) employed as starting compound may be effected by reacting methyl ortho-formate with the daunomycinone derivative of the formula (Ia) in methanol, dioxane or mixed solvents of them at a temperature of 0° C. to 50° C. The compound of the formula (VII) obtained may be reacted with bromine in a halogenated hydrocarbon such as dichloromethane, a lower alkanol such as methanol, dioxane or tetrahydrofurn at a temperature of 0° C. to 50° C. to produce the compound of the formula (VIII). In order to eliminate the dimethylketal group from the compound of the formula (VIII), this compound may then be treated with hydrobromic acid or acetone, thereby affording the compound of the formula (IX).

For the hydrolysis of the bromomethyl group (—CH₂—Br) at the 14-position of the compound of the formula (IX), this compound is reacted with sodium formate or lithium formate. The reaction with sodium formate or lithium formate may be effected at a temperature of 0° to 50° C. for a reaction time of 1 to 48 hours in a solvent which may be water or dimethylsulfoxide, dimethylformamide, dioxane, an ether such as tetrahydrofuran and the like, or a ketone such as acetone and others. When formyloxy groups have occasionally been introduced into the 14-position of the reaction product through a side-reaction, the reaction product may be treated with aqueous ammonia or aqueous sodium hydrogen carbonate to achieve the hydrolytic removal of the formyloxy groups (see the modification of the Arcamone's process described in Example 1 of Japanese patent application pre-publication No. 299296/89 or U.S. Pat. No. 4,125,607). Thus, there is produced the adriamycinone derivative of the formula (Ib) according to the first aspect of this invention (see Example 2 given hereinafter).

(D) The production of the adriamycinone derivative of the formula (Ib) according to the first aspect of this invention may be conducted also by a process which comprises preparing such a protected adriamycinone derivative where the 14-hydroxyl group of adriamycinone has been protected with an appropriate hydroxyl-protecting group, preferably tertiary-butyldimethylsilyl group (abbreviated as TBS), namely a 14-O-protected adriamycinone derivative, condensing the 7-hydroxyl group of said protected adriamycinone derivative with a 3,4-di-O-protected-2,6-dideoxy-2,6,6,6-tetrafluoro-L-talopyranosyl halide of the formula (IV) shown hereinbefore, and then eliminating the remaining hydroxyl-protecting group from the resultant condensation product by a conventional deprotecting method.

According to a ninth aspect of this invention, therefore, there is provided a process for the preparation of 7-O-(2,6-dideoxy-2,6,6,6-tetrafluoro-α-L-talopyranosyl) adriamycinone represented by the following formula:

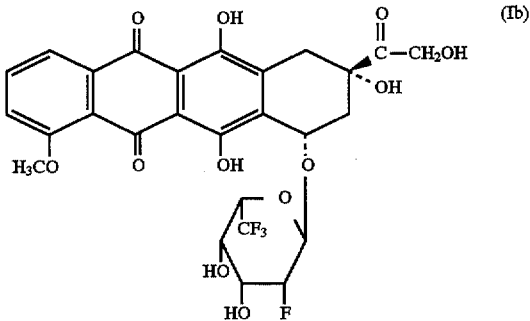

which comprises the steps of reacting a 14-O-protected adriamycinone represented by the following formula:

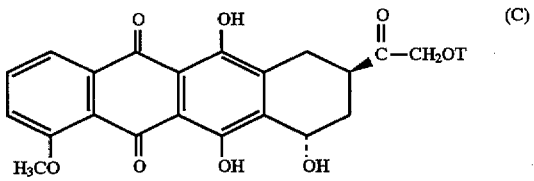

wherein T means a hydroxyl-protecting group, with a 3,4-di-O-protected 2,6-dideoxy-2,6,6,6-tetrafluoro-L-talopyranosyl halide represented by the following formula:

wherein the two Y' are simultaneously acetyl groups or benzoyl groups as a hydroxyl-protecting group and X is an iodine or bromine atom, in an organic solvent and in the presence of a condensation catalyst, to produce a 14-O-protected 7-O-(3,4-di-O-protected-2,6-dideoxy-2,6,6,6-tetrafluoro-α-L-talopyranosyl)adriamycinone represented by the following formula:

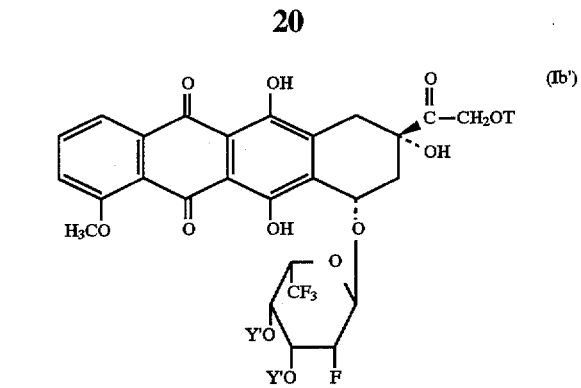

wherein T and Y' have the same meanings as defined above; and then eliminating the groups T and Y' as the hydroxyl-protecting groups remaining in the resulting condensation product of the formula (Ib') therefrom.

The hydroxyl-protecting group T present in the 14-O-protected-adriamycinone of the formula (C) above may conveniently be the aforesaid tertiary-butyldimethylsilyl group (TBS) but may also be triphenylmethyl group, p-methoxyphenyldiphenylmethyl group or tertiary-butyldiphenylsilyl group. This hydroxyl-protecting group T can be introduced into the 14-hydroxyl group of adriamycinone in a known manner so that the protected adriamycinone derivative of the formula (C) is prepared.

In the above-mentioned process according to the ninth aspect of this invention, it is convenient that the 14-O-protected-adriamycinone derivative of the formula (C) and a sugar halide of the formula (IV) are dissolved in an organic solvent such as dichloroethane and then condensed with each other in the presence of mercuric iodide or bromide, yellow-colored mercuric oxide and Molecular Sieve 3A as added to the resulting solution of the starting compounds, and that the α-L-condensation product of the formula (Ib') so produced is then recovered from the reaction solution, followed by eliminating the acetyl groups (or benzoyl groups) as the hydroxyl-protecting group from the α-L-condensation product by an ester-exchange reaction and also eliminating the silyl group therefrom by acid hydrolysis, so that the target Compound (Ib) is produced (see Example 3 given hereinafter).

Furthermore, the preparation of the adriamycinone derivative of the formula (II) according to the second aspect of this invention is described below.

(E) For the preparation of the 7-O-(2,6-dideoxy-6,6,6-trifluoro-α-L-lyxo-hexopyranosyl)adriamycinone represented by the formula (II) according to the second aspect of this invention, it is necessary to use 1-O-acetyl derivative of 2,6-dideoxy-6,6,6-trifluoro-α-L-lyxo-hexopyranose or 3,4-di-O-protected derivative thereof, or a 3,4-di-O-protected-2,6-dideoxy-6,6,6-tri-fluoro-α-L-lyxo-hexopyranosyl iodide or bromide which are new sugar compounds. The respective steps (1') to (12') involved in the method for the synthesis of these new sugar compounds are explained below firstly in brief. However, Referential Example 2 given hereinafter will be referred to as detailed descriptions of the reactions which are effected in the respective steps of said synthetic method.

Step (1'):

A known compound, methyl 4-deoxy-α-L-erythro-pentopyranoside [Compound (1')] of the formula

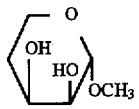

is employed and the 2- and 3-hydroxyl groups of Compound (1') are benzylated by reaction with benzyl bromide, whereby there is produced methyl 2,3-di-O-benzyl-4-deoxy-α-L-erythro-pentopyranoside [Compound (2')] of the formula

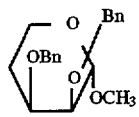

Step (2'):

Compound (2') is hydrolyzed with acid to cleave the glycoside linkage at the 1-position of said compound, whereby there is produced 2,3-di-O-benzyl-4-deoxy-L-erythro-pentopyranose [Compound (3')] of the formula

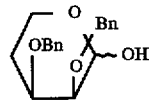

Step (3'):

Compound (3') is reacted with 1,3-propanedithiol in the presence of boron trifluoride-ethyl ether to cleave the sugar ring of Compound (3'), whereby there is produced 2,3-di-O-benzyl-4-deoxy-L-erythro-pentose trimethylene dithioacetal [Compound (4')] of the formula

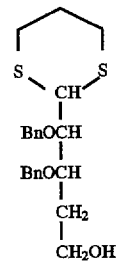

as a straight-chain compound of the dithioacetal type.

Step (4'):

The primary hydroxyl group of Compound (4') is acetylated with acetic anhydride to produce 5-O-acetyl-2,3-di-O-benzyl-4-deoxy-L-erythro-pentose trimethylene dithioacetal [Compound (5')] of the formula

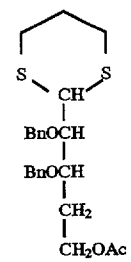

Step (5'):

Compound (5') is reacted with mercury perchlorate in aqueous tetrahydrofuran in the presence of calcium carbonate to cleave the dithioacetal ring of Compound (5'), whereby there is produced 5-O-acetyl-2,3-di-O-benzyl-4-deoxy-aldehyde-L-erythro-pentose [Compound (6')] of the formula

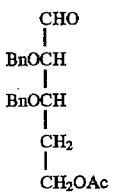

as an aldehyde-type compound.

Step (6'):

Compound (6') is then reacted with trifluoromethyl-trimethylsilane in anhydrous tetrahydrofuran in the presence of tetrabutylammonium fluoride. Thereby, there are produced 6-O-acetyl-3,4-di-O-benzyl1,5-dideoxy-1,1,1-trifluoro-L-arabino-hexitol [Compound (7')] of the formula

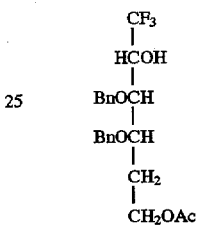

as an L-arabino-hexitol derivative having a trifluoromethyl group incorporated therein and its 2-epimer [Compound (8')] of the formula.

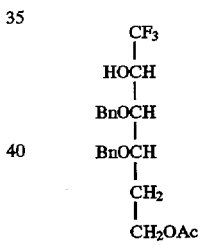

Step (7'):

Compound (7') is treated with a methanolic solution of sodium methoxide to remove the acetyl group from Compound (7'). There is thus produced 3,4-di-O-benzyl1,5-dideoxy-1,1,1-trifluoro-L-arabinohexitol [compound (9')] of the formula

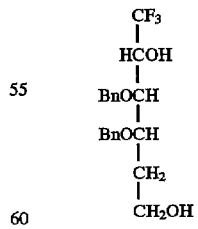

as a diol.

Step (8'):

Reactions of oxidizing selectively the primary hydroxyl group of Compound (9') and forming simultaneously the ring of a pyranose are then conducted. For this purpose, the 2- and 6-hydroxyl groups of Compound (9') are trimethylsilylated, followed by effecting Collin's oxidation of the resulting trimethylsilylated product. Thus, the primary trimethylsilyloxy group of the resulting trimethylsilylated product is subjected to selective oxidation to afford an aldehyde product. This aldehyde product is then hydrolyzed with acid to remove the remaining trimethylsilyl group and concurrently bring about the cyclization reaction, whereby there is produced 3,4-di-O-benzyl-2,6-dideoxy-6,6,6-trifluoro-L-lyxo-hexopyranose [Compound (10')] of the formula

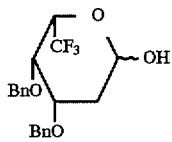

as a 2,6-dideoxy-6,6,6-trifluoro-L-lyxo-hexopyranose drivative.

Step (9'):

The 1-hydroxyl group of Compound (10') is then acetylated with acetic anhydride to produce 1-O-acetyl-3,4-di-O-benzyl-2,6-dideoxy-6,6,6-trifluoro-L-lyxo-hexopyranose [Compound (11')] of the formula

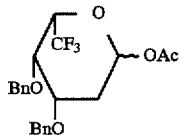

Step (10'):

The benzyl groups at the 3- and 4-positions of Compound (11') are removed therefrom by catalytic reduction to produce 1-O-acetyl-2,6-dideoxy-6,6,6-trifluoro-L-lyxo-hexopyranose [Compound (12')] of the formula

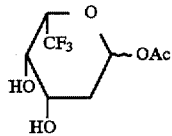

Step (11'):

The hydroxyl groups at the 3- and 4-positions of Compound (12') are acetylated with acetic anhydride, whereby there is produced 1,3,4-tri-O-acetyl-2,6-dideoxy-6,6,6-trifluoro-L-lyxo-hexopyranose [Compound (13')] of the formula

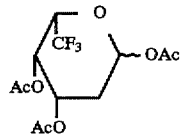

as a tri-O-acetylated product. When this Compound (13') is subjected to a silica gel column chromatographey as developed with dichloromethane, Compound (13') can be isolated separately into the α-anomer [Compound (13'-a)] and the β-anomer [Compound (13'-b)].

Step (12'):

Compound (13') (the mixture of the aforesaid anomers) is brominated in its solution in hydrogen bromide-acetic acid by conventional method, whereby there is obtained 3,4-di-O-acetyl-2,6-dideoxy-6,6,6-trifluoro-α-L-lyxo-hexopyranosyl bromide [Compound (14')] of the formula

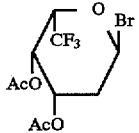

as a 1-bromo sugar. While, when Compound (13') is reacted with iodotrimethylsilane in anhydrous toluene, there is produced a corresponding 1-iodo sugar.

The above Compound (10'), Compound (11'), Compound (12') and Compound (13') are new compounds. When Compound (10') or Compound (11') is reduced with hydrogen in the presence of a palladium catalyst in a conventional manner, it is feasible to remove the 3- and 4-benzyl groups of these compounds therefrom, whereby there can be produced 2,6-dideoxy-6,6,6-trifluoro-L-lyxo-hexopyranose or 1-O-acetyl-2,6-dideoxy-6,6,6-trifluoro-L-lyxo-hexopyranose. After the removal of the benzyl groups, it is also possible to introduce another optionally appropriate hydroxyl-protecting groups into the resulting debenzylated product with aid of such methods for protecting hydroxyl group which are known in the chemistry of sugar.

According to another aspect of this invention, therefore, there is provided a 3,4-di-O-protected- or unprotected-2,6-dideoxy-6,6,6-trifluoro-L-lyxo-hexopyranose or 1-O-acetyl derivative thereof, which is represented by the following general formula:

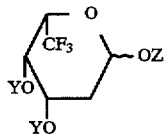

(X)

wherein the two Y are simultaneously hydrogen atoms or are simultaneously benzyl groups or acetyl groups as a hydroxyl-protecting group and Z is a hydrogen atom or an acetyl group.

As described in the above, Compound (14') is produced from Compound (13') by the bromination, and similarly from Compound (13') may be produced a corresponding 1-iodo sugar by reaction with an appropriate iodination agent. In place of the benzyl groups or acetyl groups which protect the 3- and 4-hydroxyl groups of Compound (11') and Compound (13'), another appropriate hydroxyl-protecting groups, for example, benzoyl group, may have been introduced thereinto.

According to a further another aspect of this invention, therefore, there is provided a 3,4-di-O-protected-2,6-dideoxy-6,6,6-trifluoro-α-L-lyxo-hexopyranosyl halide represented by the following general formula:

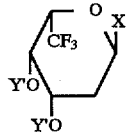

(XI)

wherein the two Y' are simultaneously acetyl groups or benzoyl groups as a hydroxyl-protecting group and X is an iodine or bromine atom.

The adriamycinone derivative of the formula (II) according to the second aspect of this invention may also be produced by a process which comprises a step of condensing a 3,4-di-O-protected-2,6-dideoxy-6,6,6-trifluoro-α-L-lyxo-hexopyranosyl halide of the general formula (XI) mentioned hereinbefore, with the 7-hydroxyl group of a 14-O-protected-adriamycinone of the formula (C) used in the process of the ninth aspect of this invention.

According to a still further aspect of this invention, therefore, there is provided a process for the preparation of 7-O-(2,6-dideoxy-6,6,6-trifluoro-α-L-lyxo-hexopyranosyl) adriamycinone represented by the following formula:

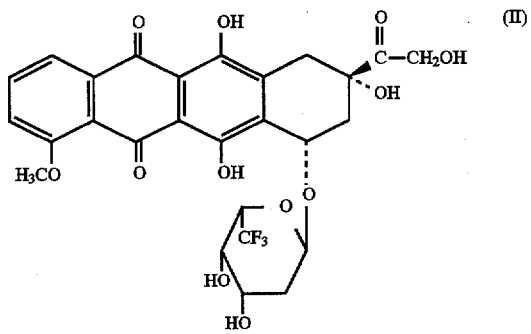

which comprises the steps of reacting a 14-O-protected adriamycinone represented by the following formula:

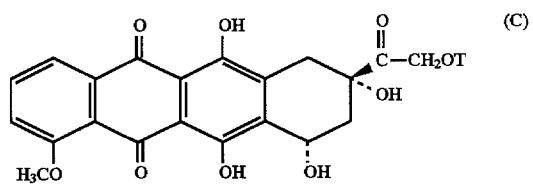

wherein T means a hydroxyl-protecting group, with a 3,4-di-O-protected-2,6-dideoxy-6,6,6-trifluoro-α-L-lyxo-hexopyranosyl halide represented by the following formula:

wherein the two Y' groups are simultaneously acetyl groups or benzoyl groups as a hydroxyl-protecting group and X is an iodine or bromine atom, in an organic solvent and in the presence of a condensation catalyst, to produce a 14-O-protected 7-O-(3,4-di-O-protected-2,6-dideoxy-6,6,6-trifluoro-α-L-lyxo-hexopyranosyl)adriamycinone represented by the following formula:

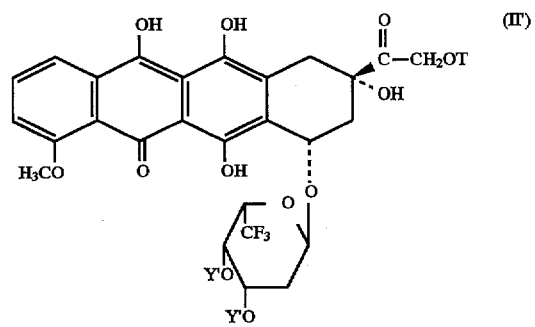

wherein T and Y' have the same meanings as defined above, and then eliminating the groups T and Y' as the hydroxyl-protecting groups remaining in the resulting condensation product of the formula (II') therefrom.

The above-described process for the preparation of the adriamycinone derivative of the formula (II) may be conducted in the same manner as the process of the ninth aspect of this invention as stated hereinbefore (see Example 4 given hereinafter).

This invention is now further illustrated by the following Referential Examples 1 and 2 and Examples 1 to 4. Referential Examples 1–2 illustrate the synthesis of various 2,6-dideoxy-2,6,6,6-tetrafluoro-α-L-talopyranose derivatives and the synthesis of various 2,6-dideoxy-6,6,6-trifluoro-L-lyxo-hexopyranose derivatives. Examples 1–4 illustrate the synthesis of the novel anthracycline derivatives of formulae (Ia) and (Ib) and the synthesis of the adriamycinone derivative of formula (II) according to this invention. In all the formulae given in these Referential Examples and Examples, Bn means benzyl group and Ac means acetyl group.

Referential Example 1

(1) Preparation of methyl 4-deoxy-4-fluoro-β-L-ribopyranoside (Compound 2)

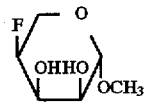

Methyl α-D-lyxopyranoside (Compound 1) (see F. P. Phelps et. al, "Journal of American Chemical Society" Vol. 48, pp. 503–507, 1926) (8.27 g) was suspended in anhydrous dichloromethane (167 ml) and the suspension was cooled to −40° C. To the suspension was added diethylaminosulfur trifluoride (26.8 ml), and then the reaction mixture was stirred at room temperature for 1 hour to conduct the fluorination reaction.

The resulting reaction solution was cooled to −20° C., to which methanol (170 ml) was added and the resulting mixture was stirred at room temperature for 15 hours. The reaction solution was neutralized with addition of sodium hydrogen carbonate (105 g) and the insoluble matters was removed by filtration. The filtrate was concentrated under a reduced pressure and the residue so obtained was purified by a silica gel column chromatography (developer: chloroform-acetone, 7:1), affording the titled Compound (2) as a syrup (7.54 g, yield 90%).

$^1$H-NMR spectrum (in deutero-chloroform): δ 4.79 (1H, d, H-1) 4.74 (1H, br d, H-4) 3.42 (3H, s, OCH$_3$)

$^{19}$F-NMR spectrum (in deutero-chloroform, CFCl$_3$ as internal standard): δ 203.0 (ddddd, J$_{3,F}$=30, J$_{4,F}$=49, J$_{5ax,F}$=38, J$_{5 eq,F}$=15.5, J$_{F,OH-2}$=8 Hz)

(2) Preparation of methyl 2,3-di-O-benzyl-4-deoxy-4-fluoro-α-L-ribopyranoside (Compound 3)

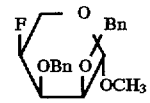

Compound (2) obtained in the above item (1) (7.44 g) was dissolved in anhydrous N,N-dimethylformamide (DMF) (72 ml), to which was then added a 60% sodium hydride (9.4 g) in oil. The mixture was stirred at room temperature for 1 hour. To the reaction mixture was added benzyl bromide (16 ml) under ice-cooling, and the resulting mixture was stirred at room temperature for 2 hours to conduct the O-benzylation.

The reaction solution was poured into a 3% aqueous acetic acid solution (500 ml) and the resulting mixture was extracted with chloroform. The chloroform solution obtained was washed with a saturated aqueous sodium hydrogen carbonate solution and a saturated aqueous sodium chloride solution in order. Thereafter, the solution thus washed was dried over anhydrous sodium sulfate and concentrated under a reduced pressure. The resulting residue was purified by a silica gel column chromatography (developer: toluene-ethyl acetate, 30:1), affording the titled Compound (3) as a syrup (12.61 g, yield 81%).

$^1$H-NMR spectrum (in deutero-chloroform): δ 7.2–7.4 (10H, m, aromatic proton) 4.74 (1H, d, H-1) 4.66 (1H, ddt, H-4) 3.40 (3H, s, OCH$_3$)

$^{19}$F-NMR spectrum (in deutero-chloroform, CFCl$_3$ as internal standard): δ −202.3 (dddd, $J_{3,F}$=23.5, $J_{4,F}$=48.5, $J_{5ax,F}$=24, $J_{5eq,F}$=10 Hz)

(3) Preparation of 2,3-di-O-benzyl-4-deoxy-4-fluoro-L-ribopyranose (Compound 4)

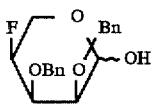

Compound (3) obtained in the above item (2) (3.06 g) was dissolved in 0.4N hydrogen chloride-80% aqueous acetic acid solution (31 ml), and the solution was allowed to stand at 80° C. for 3.5 hrs. to conduct the reaction (for the cleavage of the glycoside linkage by hydrolysis).

The resulting reaction solution was poured into water (200 ml) containing sodium hydrogen carbonate (38 g), and the mixture thus obtained was extracted with chloroform. Then, the chloroform solution obtained was washed with a saturated aqueous sodium hydrogen carbonate solution and a saturated aqueous sodium chloride solution in order. The solution thus washed was dried over anhydrous sodium sulfate and the dried solution was concentrated under a reduced pressure. The resulting residue was purified by a silica gel column chromatography (developer: hexane-ethyl acetate, 5:2), thus yielding the titled Compound (4) which was a mixture of α-anomer and β-anomer as a syrup (2.58 g, yield 88%).

$^{19}$F-NMR spectrum (in deutero-chloroform): δ −202.6 (dddd, F-4 of β-anomer) −199.2 (br d, F-4 of α-anomer)

(4) Preparation of 2,3-di-O-benzyl-4-deoxy-4-fluoro-L-ribose trimethylene dithioacetal (Compound 5)

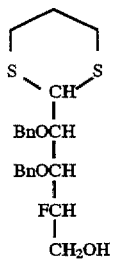

Compound (4) obtained in the item (3) (4.12 g) was dissolved in anhydrous dichloromethane (76 ml). To the solution were added 1,3-propanedithiol (2.1 ml) and boron trifluoride-diethyl ether (0.53 ml). The resulting reaction mixture was stirred at room temperature for 2 hrs. to conduct the reaction.

The reaction solution was diluted with chloroform, washed with a 5% aqueous sodium hydroxide solution and water in order and dried over anhydrous sodium sulfate. The solution thus dried was concentrated under a reduced pressure. The resulting residue was purified by a silica gel column chromatography (developer: toluene-ethyl acetate, 12:1→4:1, by gradient method), thus giving the titled compound (5) as a syrup (3.92 g, yield 75%).

$^1$H-NMR spectrum (in deutero-chloroform): δ 4.42 (1H, d, H-1) 2.5–2.9 (4H, m, thioacetal) 2.0–2.15 (1H, m, thioacetal) 1.8–2.0 (1H, m, thioacetal)

$^{19}$F-NMR spectrum (in deutero-chloroform, CFCl$_3$ as internal standard): δ −195.6 (ddt, $J_{3,F}$=14, $J_{4,F}$=46, $J_{5a,F}$=$J_{5b,F}$=24 Hz)

(5) Preparation of 5-O-acetyl-2,3-di-O-benzyl-4-deoxy-4-fluoro-L-ribose trimethylene dithioacetal (Compound 6)

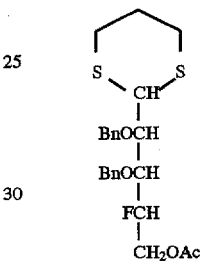

Compound (5) obtained in the item (4) (2.40 g) and acetic anhydride (2.7 ml) were dissolved in anhydrous pyridine (24 ml) and the solution was allowed to stand at room temperature for 3 hrs. to conduct the O-acetylation reaction.

The reaction solution was poured into water (250 ml) and the mixture was stirred for 1.5 hrs. and then extracted with chloroform. The resulting chloroform solution was washed with a 20% aqueous potassium hydrogen sulfate solution, a saturated aqueous sodium hydrogen carbonate solution and water in order. Then, the solution thus washed was dried over anhydrous sodium sulfate and concentrated under a reduced pressure, thereby yielding the titled Compound (6) as a syrup (2.64 g) which was a quantitative yield.

$^1$H-NMR spectrum (in deutero-chloroform): δ 4.2–4.4 (2H, m, H-5a, 5b) 2.05 (3H, s, OAc)

$^{19}$F-NMR spectrum (in deutero-chloroform, CFCl$_3$ as internal standard): δ −193.0 (dddd).

(6) Preparation of 5-O-acetyl-2,3-di-O-benzyl-4-deoxy-4-fluoro-aldehyde-L-ribose (Compound 7)

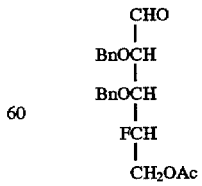

Compound (6) obtained in the item (5) (2.58 g) was dissolved in a mixture (34 ml) of tetrahydrofuran (THF)—water (10:3). To the solution were added calcium carbonate (10.24 g) and a THF solution (20 ml) of mercury perchlorate trihydrate (6.01 g). The mixture was stirred at room temperature for 2 hrs. To the reaction solution was further added a THF solution (6 ml) of mercury perchlorate trihydrate (0.57 g), and the resultant mixture was stirred for 30 minutes to conduct the oxidation reaction.

The resulting reaction mixture was filtered to remove insoluble matters and the filtrate was diluted with dichloromethane. A saturated aqueous sodium hydrogen carbonate solution was added to the resulting dichloromethane solution and the mixture was vigorously shaked. The insoluble matters so deposited were removed by filtration. Thereafter, the filtrate was washed with a 10% aqueous potassium iodide solution and water in order, dried over anhydrous sodium sulfate and then concentrated under a reduced pressure, thus affording the titled Compound (7) as a syrup (1.92 g, yield 92%).

$[\alpha]_D^{23}$ −62° (c 1, chloroform)

$^1$H-NMR spectrum (in deutero-chloroform): δ 9.65 (1H, br d, H-1) 2.01 (3H, s, OAc)

$^{19}$F-NMR spectrum (in deutero-chloroform, CFCl$_3$ as internal standard: δ −194.7 (ddddd, $J_{1,F}$=4, $J_{3,F}$=6, $J_{4,F}$=46, $J_{5a,F}$=29, $J_{5b,F}$=26 Hz).

(7) Preparation of 6-O-acetyl-3,4-di-O-benzyl-1,5-dideoxy-1,1,1,5-tetrafluoro-L-altritol (Compound 8)

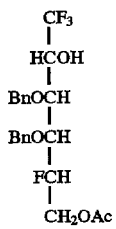

Compound (7) obtained in the item (6) (1.87 g) and trifluoromethyltrimethylsilane (1.2 ml) were dissolved in anhydrous THF (15 ml), to which was added a THF solution (3.6 ml) of tetrabutylammonium fluoride trihydrate (160 mg) under ice cooling. The resulting mixture was allowed to stand at room temperature for 1 hour (for the introduction reaction of trifluoromethyl group).

After concentrating, the reaction solution was diluted with chloroform, and the diluted solution was washed with water, dried over anhydrous sodium sulfate and concentrated under a reduced pressure. The syrup thus obtained was dissolved in an 80% aqueous acetic acid (20 ml) and the solution was allowed to stand at 50° C. for 3 hrs, whereby the trimethylsilyloxy group as formed during the above-mentioned reaction was converted into hydroxyl group. The resulting reaction solution was concentrated under a reduced pressure to leave a residue which was then subjected to a silica gel column chromatography (developer: toluene-ethyl acetate, 30:1) for the isolation and purification of the desired compound. There were thus obtained the titled Compound (8) (0.65 g, yield 29%) and its 2-epimer (Compound 9) (0.87 g, yield 39%) each as a syrup.

$[\alpha]_D^{19}$ −21° (c 1.4, chloroform)

$^1$H-NMR spectrum (in deutero-chloroform): δ 4.92 (1H, ddt, H-5) 4.17 (1H, dq, H-2) 2.08 (3H, s, OAc)

$^{19}$F-NMR spectrum (in deutero-chloroform, CFCl$_3$ as internal standard): δ −193.3 (1F, m, F-5) −77.0 (3F, d, CF$_3$).

(8a) Preparation of 3,4-di-O-benzyl1,5-dideoxy-1,1,1,5-tetrafluoro-L-altritol (Compound 10)

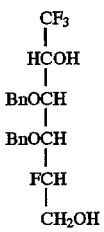

Compound (8) obtained in the item (7), i.e. 6-O-acetyl-3,4-di-O-benzyl-1,5-dideoxy-1,1,1,5-tetrafluoro-L-altritol, (0.62 g) was dissolved in a methanolic solution (17 ml) of 0.02N sodium methoxide. The solution obtained was allowed to stand at room temperature for 20 minutes to conduct the reaction for elimination of O-acetyl group.

After neutralizing the reaction solution by addition of a strongly acidic ion exchange resin, Dowex 50W (H$^+$ type), to the solution, the resin was filtered off and the filtrate was concentrated under a reduced pressure. The resulting residue was recrystallized from chloroformhexane to afford the titled Compound (10) as needles (0.52 g, yield 93%).

Melting point 64°–65° C.

$[\alpha]_D^{23}$ −29° (c 1 chloroform)

(8b) Preparation of 1,5-dideoxy-1,1,1,5-tetrafluoro-L-altritol (Compound 10a)

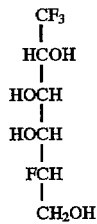

Compound (10) obtained in the item (Sa), i.e. 3,4-di-O-benzyl-1,5-dideoxy-1,1,1,5-tetrafluoro-L-altritol (0.11 g) was dissolved in a mixture of dioxane-acetic acid-water (10:1:1) (3 ml), to which palladium black was added and then hydrogen gas was blown into the solution to effect the catalytic reduction for 3 hrs.

The reaction mixture was filtered and the filtrate was concentrated under a reduced pressure, yielding the titled Compound (10a) as a solid, quantitatively (0.06 g).

$^{19}$F-NMR spectrum (in deutero-methanol, CFCl$_3$ as internal standard): δ −195 (1F, F-5) −77 (3F, CF$_3$)

(9) Preparation of 3,4-di-O-benzyl-2,6-dideoxy-2,6,6,6-tetrafluoro-α-L-talopyranose (Compound 11)

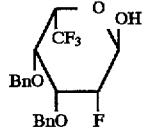

Compound (10) obtained in the item (8a) (0.73 g), chlorotrimethylsilane (1.4 ml) and 4-dimethylaminopyridine (0.12 g) were dissolved in anhydrous pyridine (7 ml). The resulting solution was allowed to stand at room temperature for 15 hrs. to effect the trimethylsilylation reaction of the 2- and 6-hydroxyl groups. The reaction solution obtained was diluted with ethyl acetate, washed with water, dried over anhydrous sodium sulfate and then concentrated under a reduced pressure, affording 2,6-di-O-trimethylsilylated product as a syrup (994 mg).

The next step was to conduct the selective oxidation reaction of the 6-trimethylsilyloxy group. Thus, anhydrous chromic acid (1.29 g) was suspended in a mixture of anhydrous dichloromethane (36 ml) and anhydrous pyridine (2.2 ml) and the suspension was stirred at room temperature for 30 minutes. The reddish yellow liquid so obtained was cooled with ice. To the ice-cooled liquid was added a dichloromethane solution (5 ml) of the above-mentioned syrup, and the mixture obtained was stirred under ice-cooling for 2 hrs. The resulting reaction mixture was filtered through a short column packed with silica gel. The column was washed with ethyl acetate and the eluate from the column was concentrated under a reduced pressure to give a syrup (0.68 g).

Then, in order to remove the remaining trimethylsilyl group and to cause the cyclization reaction, the resulting syrup (0.68 g) was dissolved in a mixture (8 ml) of dioxane and water (9:1) containing 0.1N hydrogen chloride. The resulting solution was allowed to stand at room temperature for 1.5 hrs. to conduct the reaction. To the reaction solution was added a saturated aqueous solution of sodium hydrogen carbonate, and the resulting mixture was extracted with dichloromethane. The dichloromethane solution so obtained was washed with water, dried over anhydrous sodium sulfate and then concentrated under a reduced pressure, affording the titled Compound (11) as a syrup (0.48 g, yield 64%).

$^1$H-NMR spectrum (in deutero-chloroform): δ 5.55 (1H, br d, H-1) 4.72 (1H, br d, H-2)

$^{19}$F-NMR spectrum (in deutero-chloroform-heavy water, CFCl$_3$ as internal standard): δ −203.5 (1F, ddd, F-2, $J_{1,F}$=9, $J_{2,F}$=49 $J_{3,F}$=32 Hz), −73.5 (3F,d, CF$_3$)

(10) Preparation of 1-O-acetyl-3,4-di-O-benzyl-2,6-dideoxy-2,6,6,6-tetrafluoro-α-L-talopyranose (Compound 12)

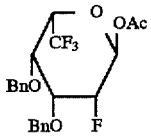

Compound (11) obtained in the item (9) (0.48 g) and acetic anhydride (0.56 ml) were dissolved in anhydrous pyridine (10 ml), and the resulting solution was allowed to stand at room temperature for 40 minutes to conduct the acetylation.

Water (0.6 ml) was added to the resulting reaction solution and the resultant mixture was concentrated to a half volume under a reduced pressure and then diluted with chloroform. The diluted solution was washed successively with a 20% aqueous potassium hydrogen sulfate solution, a saturated aqueous sodium hydrogen carbonate solution and water. Then, the solution was dried over anhydrous sodium sulfate and concentrated under a reduced pressure, to afford the titled Compound (12) as a syrup (0.47 g, yield 87%).

$^1$H-NMR spectrum (in deutero-chloroform): δ 6.46 (1H, dd, H-1) 4.69 (1H, ddt, H-2) 2.08 (3H, s, OAc)

(11) Preparation of 1-O-acetyl-2,6-dideoxy-2,6,6,6-tetrafluoro-α-L-talopyranose (Compound 13)

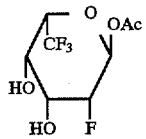

Compound (12) obtained in the item (10) (0.47 g) was dissolved in a mixture of dioxane-acetic acid-water (10:1:1) (15 ml). To the solution was added palladium black and then hydrogen gas was blown into the solution to conduct the catalytic reduction of Compound (12) for 4.5 hrs.

The reaction solution obtained was filtered and the filtrate was concentrated under a reduced pressure to yield Compound (13) quantitatively as a solid (0.28 g).

$^1$H-NMR spectrum (in deutero-chloroform): δ 6.21 (1H, dd, H-1) 4.50 (1H, dddd, H-2) 2.03 (3H, s, OAc)

(12) Preparation of 1,3,4-tri-O-acetyl-2,6-dideoxy-2,6,6,6-tetrafluoro-α-L-talopyranose (Compound 14)

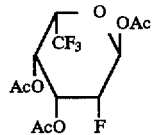

Compound (13) obtained in the item (11) (0.27 g) and acetic anhydride (1 ml) were dissolved in anhydrous pyridine (5 ml), and the solution was allowed to stand at room temperature for 20 hrs. to effect the O-acetylation reaction.

Post treatment of the reaction solution was carried out in the same manner as in Referential Example 1 (10), whereby the titled Compound (14) was obtained as a syrup (0.32 g, yield 89%).

$^1$H-NMR spectrum (in deutero-chloroform): δ 6.48 (1H, br d, H-1) 5.67 (1H, br d, H-4) 5.19 (1H, dt, H-3) 2.18, 2.15,2.12 (each 3H, s, OAc)

(13) Preparation of 3,4-di-O-acetyl-2,6-dideoxy-2,6,6,6-tetrafluoro-L-talopyranosyl iodide (Compound 15)

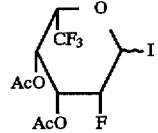

Compound (14) obtained in the item (12), i.e. 1,3,4-tri-O-acetyl-2,6-dideoxy-2,6,6,6-tetrafluoro-α-L-talopyranose (195 mg) was dissolved in anhydrous toluene (4 ml). To the solution was added iodotrimethylsilane (0.5 ml), and the resultant mixture was allowed to stand in a dark place at 80° C. for 15 hrs. to conduct the iodination reaction.

The reaction solution so obtained was diluted with toluene, washed with a 10% aqueous sodium thiosulfate solution, a saturated aqueous sodium hydrogen carbonate solution and water in order. The reaction solution so washed was dried over anhydrous sodium sulfate and concentrated under a reduced pressure. The residue obtained was purified by a flash silica gel column chromatography (developer: hexane-ethyl acetate, 6:1), to give the titled Compound (15) as a syrup (132 mg, yield 58%).

$^1$H-NMR spectrum (in deutero-chloroform): δ 7.01 (1H, br d, H-1) 2.14, 2.11 (each 3H, s, OAc)

$^{19}$F-NMR spectrum (in deutero-chloroform, CFCl$_3$ as internal standard): δ −173.6 (1F, ddd, F-2) −73.8 (3F, d, CF$_3$)

Referential Example 2

(1) Preparation of methyl 2,3-di-O-benzyl-4-deoxy-β-L-erythro-pentopyranoside (Compound 2')

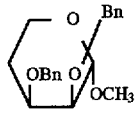

A 60% sodium hydride (7.7 g) in oil was suspended in anhydrous N,N-dimethylformamide (DMF) (13 ml). To the suspension was added methyl 4-deoxy-β-L-erythro-pentopyranoside (Compound 1') (P. W. Kent and P. F. V. Ward, "Journal of the Chemical Society" pp. 416–418, 1953) (5.63 g) in an anhydrous DMF solution (20 ml). After the resulting mixture was stirred at room temperature for 50 minutes, benzyl bromide (13.6 ml) was added under ice-cooling, and the mixture so obtained was further stirred at room temperature for 40 minutes to conduct the reaction (for O-benzylation).

To the resulting reaction solution, acetic acid (13.6 ml) and then water (300 ml) were added, and the solution thus diluted was extracted with chloroform. The chloroform solution obtained was washed with a saturated aqueous sodium hydrogen carbonate solution and water, successively, and then dried over anhydrous sodium sulfate and concentrated under a reduced pressure. Xylene was added to the resulting residue and the resulting solution was concentrated under a reduced pressure. Repetition of this step was made for the removal of DMF. The residue so obtained was purified by a silica gel column chromatography (developer: toluene-acetone, 30:1), to afford the titled Compound (2') as a syrup (10.1 g, yield 81%).

$[α]_D^{23}$+35° (c 19 chloroform)

Elemental analysis (for C$_{20}$H$_{24}$O$_4$): Calculated: C, 73.15; H, 7.37% Found: C, 73.08 ; H, 7.24%

(2) Preparation of 2,3-di-O-benzyl-4-deoxy-L-erythropentopyranose (Compound 3')

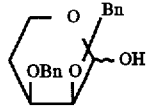

Compound (2') obtained in the above item, (1) i.e. methyl 2,3-di-O-benzyl-4-deoxy-β-L-erythro-pentopyranoside (4.81 g) was dissolved in a mixture (48 ml) of 2N hydrochloric acid-acetic acid (1:4), and the solution obtained was allowed to stand at 80° C. for 40 minutes to effect the hydrolysis (for the cleavage of the glycoside bond).

The resulting reaction solution was poured into water (400 ml) containing sodium hydrogen carbonate (74 g), and the mixture obtained was extracted with chloroform. The chloroform solution thus obtained was washed with a saturated sodium hydrogen carbonate solution and water, successively, and then dried over anhydrous sodium sulfate and concentrated under a reduced pressure. The resulting residue was purified by a silica gel column chromatography (developer: toluene-acetone, 12:1). The titled Compound (3') was obtained in the form of a mixture of α-anomer and β-anomer as a syrup (3.78 g, yield 82%).

$^1$H-NMR spectrum (in deutero-chloroform): δ 5.07 (0.5H, br s, H-1) 5.20 (0.5H, t, H-1 of the other anomer)

(3) Preparation of 2,3-di-O-benzyl-4-deoxy-L-erythropentose trimethylene dithioacetal (Compound 4')

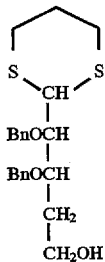

Compound (3') obtained in the item (2), i.e. 2,3-di-O-benzyl-4-deoxy-L-erythro-pentopyranose (10.28 g) was dissolved in anhydrous dichloroethane (60 ml). To the solution were added 1,3-propanedithiol (5.9 ml) and boron trifluoride-diethylether (1.2 ml). The resulting reaction mixture was stirred at 60° C. for 3.5 hrs. to conduct the reaction. The reaction solution thus obtained was diluted with chloroform, washed with a 5% aqueous sodium hydroxide solution and water, successively, and then dried over anhydrous sodium sulfate and concentrated under a reduced pressure. The resulting residue was purified by a silica gel column chromatography (developer: toluene-acetone, 12:1), to yield the titled Compound (4') as a syrup (8.50 g, yield 64%).

$[α]_D^{25}$−39° (c 1, chloroform)

Elemental analysis (for C$_{22}$H$_{28}$O$_3$S$_2$): Calculated: C, 65.41; H, 6.98 ; S, 15.85% Found: C, 65.41 ; H, 6.95 ; S, 15.78%

(4) Preparation of 5-O-acetyl-2,3-di-O-benzyl-4-deoxy-L-erythropentose trimethylene dithioacetal (Compound 5')

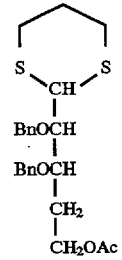

Compound (4') obtained in the item (3), i.e. 2,3-di-O-benzyl-4-deoxy-L-erythro-pentose trimethylene dithioacetal (1.03 g) and acetic anhydride (0.4 ml) were dissolved in anhydrous pyridine (8 ml), and the solution thus obtained was allowed to stand at room temperature for 23 hrs. to effect the O-acetylation. Then, water (0.4 ml) was added to the reaction solution, and the mixture was allowed to stand for 2 hrs. and then concentrated under a reduced pressure.

To the residue obtained was added a 20% aqueous potassium hydrogen sulfate solution, and the mixture was extracted with chloroform. The chloroform solution obtained was washed with a saturated aqueous sodium hydrogen carbonate solution and water, successively, and then dried over anhydrous sodium sulfate and concentrated under a reduced pressure, to afford the titled Compound (5') as a syrup (1.09 g, yield 97%).

$[\alpha]_D^{21}$ −38° (c 0.7, chloroform)

$^1$H-NMR spectrum (in deutero-chloroform): δ 1.98 (3H, s, OAc)

(5) Preparation of 5-O-acetyl-2,3-di-O-benzyl-4-deoxy-aldehyde-L-erythro-pentose (Compound 6')

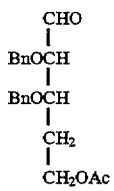

Compound (5') obtained in the item (4) above, i.e. 5-O-acetyl-2,3-di-O-benzyl-4-deoxy-L-erythro-pentose trimethylene dithioacetal (1.09 g) was dissolved in a mixture (15 ml) of tetrahydrofuran (THF)-water (10:3). To the resultant solution were added calcium carbonate (4.7 g) and a THF solution (9 ml) of mercury perchlorate trihydrate (2.9 g). The resultant the mixture was stirred at room temperature for 1 hour.

The reaction solution was diluted with addition of dichloromethane (50 ml) and a saturated aqueous sodium hydrogen carbonate solution (20 ml), and the mixture obtained was filtered through Celite to remove insoluble matters to obtain the filtrate. The residue was further washed with dichloromethane three times (30 ml each) and the washings were combined with the filtrate above.

The solution combined was washed with a saturated sodium hydrogen carbonate solution (10 ml) added. The dichloromethane solution thus obtained was washed with a aqueous potassium iodide solution and water, in order, and then dried over anhydrous sodium sulfate and concentrated under a reduced pressure, to yield the titled compound (6') (0.87 g), quantitatively.

$[\alpha]_D^{20}$ −71° (c 1, chloroform)

$^1$H-NMR spectrum (in deutero-chloroform): δ 9.71 (1H, d, CHO)

(6) Preparation of 6-O-acetyl-3,4-di-O-benzyl-1,5-dideoxy-1,1,1-trifluoro-L-arabino-hexitol (Compound 7')

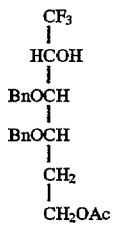

Compound (6') obtained in the item (5) above, i.e. 5-O-acetyl-2,3-di-O-benzyl-4-deoxy-aldehyde-L-erythropentose (0.81 g) and trifluoromethyltrimethylsilane (0.5 ml) were dissolved in THF (8 ml), to which was then added a THF solution (2 ml) of tetrabutylammonium fluoride trihydrate (71 mg) under ice-cooling. The resulting mixture was allowed to stand at room temperature for 1.5 hrs. to conduct the reaction (for the introduction of trifluoromethyl group).

The reaction soution was concentrated under a reduced pressure and was diluted with chloroform, washed with water, dried over anhydrous sodium sulfate and concentrated under a reduced pressure. The resulting syrup was dissolved in an 80% aqueous acetic acid (4 ml) and the solution was allowed to stand at 50° C. for 1.5 hrs. so that the 2-trimethylsilyloxy group as formed during the above reaction was converted into hydroxyl group. The resulting reaction solution was concentrated under a reduced pressure and the residue thus obtained was subjected to a silica gel column chromatography (developer: toluene-ethyl acetate, 25:1) for the purpose of separation and purification, to afford the titled (Compound 7') (0.36 g, yield 37%) and 2-epimer thereof (Compound 8') (0.36 g, yield 37%), respectively, as a syrup.

$[\alpha]_D^{24}$ −240° (c 1, chloroform)

$^{19}$F-NMR spectrum (in deutero-chloroform, CFCl$_3$ as internal standard): δ −77.6 (d, CF$_3$)

(7) Preparation of 3,4-di-O-benzyl-1,5-dideoxy1,1,1-trifluoro-L-arabino-hexitol (Compound 9')

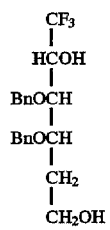

Compound (7') obtained in the item (6) above, i.e. 6-O-acetyl-3,4-di-O-benzyl-1,5-dideoxy-1,1,1-trifluoro-L-arabino-hexitol (296 mg) was dissolved in a methanolic solution (5 ml) of 0,025N sodium methoxide. The resulting solution was allowed to stand at room temperature for 1 hour to effect the elimination of the O-acetyl group. The reaction solution obtained was neutralized with addition of a strongly acidic ion exchange resin, Dowex 50W (H$^+$ form), thereto, and the resin used was filtered off. The resulting filtrate was concentrated under a reduced pressure, to afford the titled Compound (9') as a syrup (266 mg, yield 99%).

$[]\alpha_D^{21}$ −17° (c 0 7, chloroform)

$^{19}$F-NMR (deutero-chloroform, CFCl$_3$ as internal standard): δ −75.7 (d, CF$_3$)

(8) Preparation of 3,4-di-O-benzyl-2,6-dideoxy-6,6,6-trifluoro-L-lyxo-hexopyranose (Compound 10')

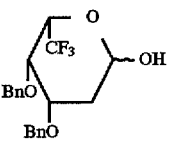

Compound (9') obtained in the item (7) above, i.e. 3,4-di-O-benzyl-1,5-dideoxy-1,1,1-trifluoro-L-arabinohexitol (1.46 g), chlorotrimethylsilane (1.7 ml) and 4-dimethylaminopyridine (0.18 g) were dissolved in anhydrous pyridine (15 ml). The resulting solution was allowed to stand at room temperature for 15 hrs. to effect the trimethylsilylation of the 2- and 6-hydroxyl groups. The resulting reaction solution was concentrated under a reduced pressure, and the concentrate obtained was diluted with ethyl acetate and washed with water. The solution so washed was dried over anhydrous sodium sulfate and concentrated under a reduced pressure, to afford the 2,6-di-O-trimethylsilylated product as a syrup (2.07 g).

The next step was to carry out the selective oxidation reaction of the 6-trimethylsilyloxy group of the trimethylsilylation product obtained as above. Thus, anhydrous chromic acid (1.82 g) suspended in a mixture of anhydrous dichloromethane (25 ml) and anhydrous pyridine (3 ml), and the resulting suspension was stirred at room temperature for 30 minutes. The resulting red liquid was cooled with ice, to which was added a dichloromethane solution (3.5 ml) of the syrupy trimethylsilylated product above. The mixture was stirred under ice-cooling for 40 minutes. The resulting reaction solution was diluted with ethyl acetate and filtered through a glass filter packed with silica gel to obtain the filtrate. The filter used was washed with ethyl acetate, and said filtrate and the washings were combined together and the mixture was concentrated under a reduced pressure. To the residue was added ethyl acetate, and the resulting insoluble matters were filtered and washed in the same manner as above. The resulting filtrate and washings were combined and the mixture was concentrated under a reduced pressure, thus yielding a syrup (1.83 g) which was an aldehyde.

The next step was to remove the remaining trimethylsilyl group and also to effect the cyclization reaction. Thus, the syrup obtained as above (1.83 g) was dissolved in a mixture (18 ml) of dioxane-water (10:1) (18 ml) containing 0.1N hydrogen chloride. The resultant solution was allowed to stand at room temperature for 50 minutes to conduct the reaction. To the reaction solution was added a saturated aqueous sodium hydrogen carbonate solution (60 ml), and the mixture was extracted with dichloromethane. The resulting dichloromethane solution was washed with water, dried over anhydrous sodium sulfate and concentrated under a reduced pressure, to afford the titled Compound (10') as a syrup (1.42 g, yield 98%).

$[\alpha]_D^{21}$ –72° (c 0.23, chloroform) (as determined at a time of 24 hours after the sample was dissolved in chloroform)

$^1$H-NMR spectrum (in deutero-chloroform): δ 5.54 (br, d, H-1 of α-anomer)

$^{19}$F-NMR spectrum (in deutero-chloroform, CFCl$_3$ as internal standard): δ –74.0 (~2.7F, CF$_3$ of α-anomer) –73.6 (~0.3F, CF$_3$ of β-anomer)

(9) Preparation of 1-O-acetyl-3,4-di-O-benzyl-2,6-dideoxy-6,6,6-trifluoro-L-lyxo-hexopyranose (Compound 11')

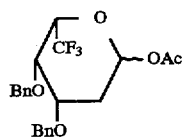

Compound (10') obtained in the item (8) above, i.e. 3,4-di-O-benzyl-2,6-dideoxy-6,6,6-trifluoro-L-lyxo-hexopyranose (1.34 g) and acetic anhydride (0.5 ml) were dissolved in anhydrous pyridine (10 ml), and the solution was allowed to stand at room temperature for 2.5 hrs. to conduct the acetylation.

Water (0.5 ml) was added to the resulting reaction solution and the mixture obtained was concentrated under a reduced pressure. The residue was diluted with chloroform and the resulting solution was washed with a 20% aqueous potassium hydrogen sulfate solution, a saturated aqueous sodium hydrogen carbonate solution and water, in order. The resulting solution so washed was dried over anhydrous sodium sulfate and concentrated under a reduced pressure, to afford the titled Compound (11'), in the form of a mixture of α-anomer and β-anomer, as a syrup (1.31 g, yield 88%).

$^1$H-NMR spectrum (in deutero-chloroform): δ 2.07, 2.11 (3H in combination, each s, OAc) 5.71 (~0.3H, dd, H-1 of β-anomer) 6.38 (~0.7H, br d, H-1 of α-anomer)

$^{19}$F-NMR spectrum (in deutero-chloroform, CFCl$_3$ as internal standard): δ –74.1 (d, CF$_3$ of α-anomer) –73.5 (d, CF$_3$ of β-anomer)

(10) Preparation of 1-O-acetyl-2,6-dideoxy-6,6,6-trifluoro-L-lyxo-hexopyranose (Compound 12')

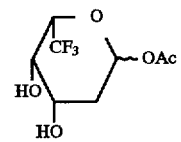

Compound (11') obtained in the item (9) above, i.e. 1-O-acetyl-3,4-di-O-benzyl-2,6-dideoxy-6,6,6-trifluoro-L-lyxo-hexopyranose (1.31 g) was dissolved in a mixture (30 ml) of dioxane-acetic acid-water (10:1:1). The solution, after the addition of palladium black thereto, was subjected to catalytic reduction by blowing hydrogen gas therein for 5 hrs. (for the debenzylation). The reaction solution obtained was filtered and the filtrate was concentrated under a reduced pressure, to afford the titled Compound (12') as a partially solidified syrup (736 mg, yield 98%).

$^1$H-NMR spectrum (in deutero-methanol): δ 5.66 (~0.3H, dd, H-1 of β-anomer) 6.15 (~0.7H, br d, H-1 of α-anomer)

$^{19}$F-NMR spectrum (in deutero-chloroform, CFCl$_3$ as internal standard): δ –73.9 (d, CF$_3$ of α-anomer) –73.4 (d, CF$_3$ of β-anomer)

(11) Preparation of 1,3,4-tri-O-acetyl-2,6-dideoxy-6,6,6-trifluoro-L-lyxo-hexopyranose (Compound 13')

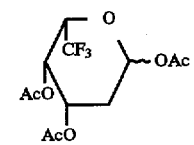

Compound (12') obtained in the item (10) above, i.e. 1-O-acetyl-2,6-dideoxy-6,6,6-trifluoro-L-lyxo-hexopyranose (0.74 g) and acetic anhydride (0.7 ml) were dissolved in anhydrous pyridine (6 ml), and the solution obtained was allowed to stand at room temperature for 20 hrs. to conduct the O-acetylation. The post-treatment of the reaction solution was carried out in the same manner as in the item (9) above, affording the titled compound, in the form of a mixture of α-anomer and β-anomer, quantitatively as a syrup (1.02 g). The Compound (13') could be separated into the α-anomer (Compound 13'-a) and the β-anomer (Compound 13'-b) as below.

(i) α-anomer, i.e. 1,3,4-tri-O-acetyl-2,6-dideoxy-6,6,6-trifluoro-α-L-lyxo-hexopyranose (Compound 13'-a):

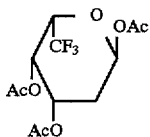

Needle crystals having melting point of 91.5°–92.5° C.
[α]$_D^{19}$ –100° (c 0.6, chloroform)
$^1$H-NMR spectrum (in deutero-chloroform): δ 2.02, 2.14, 2.15 (each 3H, s, OAc) 6.44 (1H, br d, H-1)
$^{19}$F-NMR (in deutero-chloroform, CFCl$_3$ as internal standard): δ –75.0 (d)
Elemental analysis (for C$_{12}$H$_{15}$F$_3$O$_7$): Calculated: C, 43.91 ; H, 4.61 ; F, 17.36% Found: C, 43.78 ; H, 4.67 ; F, 17.41%

(ii) β-anomer, i.e. 1,3,4-tri-O-acetyl-2,6-dideoxy-6,6,6-trifluoro-β-L-lyxo-hexopyranose (Compound 13'-b):

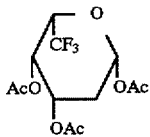

A syrup having [α]$_D^{21}$ –26° (c 0.8, chloroform):
$^1$H-NMR spectrum (in deutero-chloroform): δ 2.03 (3H, s, OAc) 2.16 (6H, s, OAc×2) 5.85 (1H, dd, H-1)
$^{19}$F-NMR spectrum (in deutero-chloroform, CFCl$_3$ as internal standard): δ –74.4 (d)

(12) Preparation of 3,4-di-O-acetyl-2,6-dideoxy-6,6,6-trifluoro-α-L-lyxo-hexopyranosyl bromide (Compound 14')

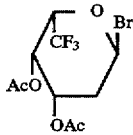

Compound (13') (the anomer mixture) as obtained in the item (11) above, i.e. 1,3,4-tri-O-acetyl-2,6-dideoxy-6,6,6-trifluoro-L-lyxo-hexopyranose (89 mg) was dissolved in a 30% hydrogen bromide-acetic acid solution (0.9 ml), and the solution obtained was allowed to stand at room temperature for 5 hrs. to conduct the bromination reaction. The reaction solution was diluted with chloroform, then washed with water, a saturated aqueous sodium hydrogen carbonate solution and water, successively, and subsequently dried over anhydrous magnesium sulfate and concentrated under a reduced pressure, to yield the titled Compound (14') as a syrup (85 mg, yield 90%).
$^1$H-NMR spectrum (in deutero-chloroform): δ 2.02, 2.14 (each 3H, s, OAc) 6.72 ! (1H, br d, H-1)
$^{19}$F-NMR spectrum (in deutero-chloroform, CFCl$_3$ as internal standard): δ 74.3 (d)

Now, the synthesis of the daunomycinone or adriamycinone derivatives of the general formula (I) according to the first aspect of this invention and the synthesis of the adriamycinone derivative of the formula (II) according to the second aspect of this invention will be illustrated by the following Examples.

Example 1

(1) Preparation of 7-O-(3,4-di-O-acetyl-2,6-dideoxy-2,6,6,6-tetrafluoro-α-L-talopyranosyl) daunomycinone [Compound (16)]

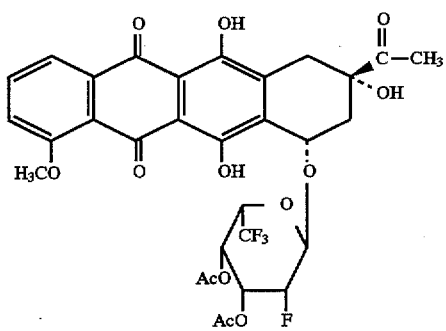

Compound (15) as obtained in Referential Example 1 (13), i.e. 3,4-di-O-acetyl-2,6-dideoxy-2,6,6,6-tetrafluoro-L-talopyranosyl iodide (130 mg), daunomycinone (178 mg), mercuric iodide (298 mg), yellow-colored mercuric oxide (617 mg) and a powder of Molecular Sieves 3A (694 mg) were suspended in anhydrous 1,2-dichloroethane (8.4 ml). The resulting mixture was stirred in a dark place at 80° C. for 9.5 hrs. to effect the condensation reaction of daunomycinone with the iodide Compound (15).

The resulting reaction solution was filtered with aid of Celite, and the filtrate was diluted with chloroform, washed with a 30% aqueous potassium iodide solution, a saturated aqueous sodium hydrogen carbonate solution and water, in order. The solution thus washed was dried over anhydrous sodium sulfate and concentrated under a reduced pressure. The residue was subjected to a silica gel column chromatography (developer: chloroform-ethyl acetate, 7:1) to effect the isolation and purification of the desired compound. The titled Compound (16) was obtained as a red solid (145 mg, yield 67%).

$^1$H-NMR spectrum (in deutero-chloroform): δ 5.75 (1H, d, H-1') 4.12 (3H, s, OMe) 2.39 (3H, s, Ac) 2.15, 2.03 (each 3H, s, OAc)

$^{19}$F-NMR spectrum (in deutero-chloroform, CFCl$_3$ as internal standard): δ –201.7 (1F, ddd, F-2') –74.1 (3F, d, CF$_3$)

(2) Preparation of 7-O-(2,6-dideoxy-2,6,6,6-tetrafluoro-α-L-talopyranosyl)daunomycinone [Compound (a) of this invention]

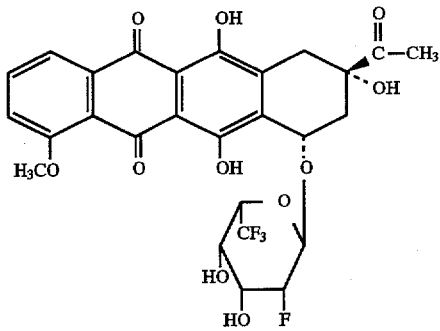

Compound (16) as obtained in Example 1 (1) above, i.e. 7-O-(3,4-di-O-acetyl-2,6-dideoxy-2,6,6,6-tetrafluoro-α-L-talopyranosyl)daunomycinone (28 mg) was suspended in a 0.2N aqueous sodium hydroxide solution (2.8 ml) and the suspension obtained was stirred at 0° C. for 3.5 hrs. to conduct the deacetylation reaction.

The reaction solution was neutralized with addition of a 1N hydrochloric acid and then extracted with chloroform. The resulting chloroform solution was washed with a saturated aqueous sodium chloride solution, dried over anhydrous sodium sulfate and concentrated under a reduced pressure, to afford the titled compound [i.e. Compound (a) according to this invention] as a red solid (23 mg, yield 94%).

$[\alpha]_D^{24}$ +138° (c 0.56, tetrahydrofuran)

$^1$H-NMR spectrum (in deutero-pyridine): δ 6.18 (1H, br d, H-1') 3.98 (3H, s, OCH$_3$) 2.58 (3H, s, Ac)

$^{19}$F-NMR spectrum (in deutero-pyridine, CFCl$_3$ as internal standard): δ −200.3 (1F, ddd, F-2') −71.9 (3F, d, CF$_3$)

Example 2

Preparation of 7-O-(2,6-dideoxy-2,6,6,6-tetrafluoro-α-L-talopyranosyl)adriamycinone [Compound (b) according to this invention]

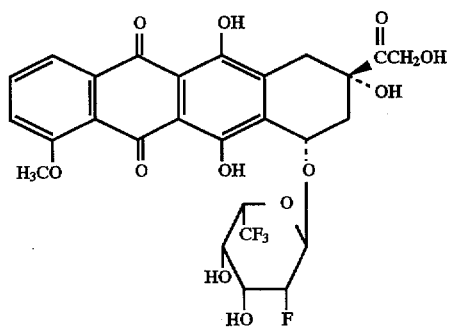

Compound (a) as obtained in Example 1 (2), i.e. 7-O-(2,6-dideoxy-2,6,6,6-tetrafluoro-α-L-talopyranosyl) daunomycinone (42 mg) and methyl orthoformate (0.06 ml) were dissolved in a mixture of anhydrous methanol (0.9 ml) and anhydrous dioxane (1.4 ml), and the resulting solution was allowed to stand at room temperature for 30 minutes to protect the 13-carbonyl group of Compound (a) by dimethylketalation.

Then, the reaction solution was cooled to 0° C. to which a solution of bromine (16 mg) in anhydrous dichloromethane (0.2 ml) was added. The resulting mixture was allowed to stand at room temperature for 2.5 hrs. to conduct the bromination of the 14-position of the daunomycinone compound.

The resulting reaction solution was concentrated under a reduced pressure to a half volume, to which hexane was added to cause precipitation of the compound of formula (VIII) above. The precipitate was taken out by centrifugal separation. The precipitate so separated was suspended in acetone (4.5 ml) and the suspension was stirred at room temperature for 2 hrs. to effect the dedimethylketalation. Upon this time, a partial introduction of isopropylidene group at the 3'- and 4'-hydroxyl groups was occurred.

Thus, a reaction solution containing the compound of formula (IX) above was obtained. This solution was concentrated under a reduced pressure, and to the residue were added acetone (2.5 ml), water (0.8 ml), tetrahydrofuran (1.1 ml) and sodium formate (66 mg). The resulting mixture was stirred at room temperature for 15 hrs. so that the 14-bromomethyl group of the compound of formula (IX) was converted into hydroxymethyl group, with a portion of the bromomethyl group being converted into formyloxymethyl group.

The resulting reaction solution was concentrated under a reduced pressure and the residue was washed with water to give a red solid (43 mg). The solid was suspended in a mixture of tetrahydrofuran (2 ml) and methanol (0.7 ml), and the suspension was cooled to 0° C., to which 1N aqueous ammonia (0.5 ml) was added. The resultant mixture was stirred at that temperature for 1 hour to eliminate the partially introduced O-formyl group of the reaction product. The reaction solution was concentrated and the residue was dissolved in an 80% aqueous acetic acid solution (2 ml). The solution was allowed to stand at 80° C. for 3 hrs. to eliminate the partially introduced 3',4'-O-isopropylidene group.

The reaction solution thus obtained was concentrated under a reduced pressure, and the residue was washed with water and then concentrated under a reduced pressure. The solid so obtained was reprecipitated from tetrahydrofuranisopropyl ether.

Thus, the titled compound [i.e. Compound (b) according to this invention] was obtained as a red solid (27 mg, yield 63%).

$[\alpha]_D^{24}$ +114° (c 0.2, tetrahydrofuran)

$^1$H-NMR spectrum (in deutero-pyridine): δ 6.15 (1H, br d, H-1') 5.42 (2H, s, H-14) 3.98 (3H, s, OCH$_3$)

$^{19}$F-NMR spectrum (in deutero-pyridine, CFCl$_3$ as internal standard): δ −200.3 (1F, ddd, F-2') −71.9 (3F, d, CF$_3$)

Example 3

(1) Preparation of 7-O-(3,4-di-O-acetyl-2,6-dideoxy-2,6,6,6-tetrafluoro-α-L-talopyranosyl)-14-O-tert-butyl-dimethylsilyladriamycinone (Compound 17)

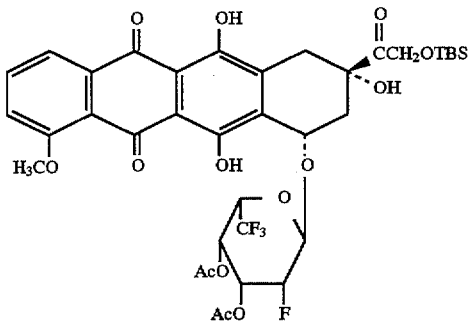

Compound (15) as obtained in Referential Example 1 (13), i.e. 3,4-di-O-acetyl-2,6-dideoxy-2,6,6,6-tetrafluoro-L-talopyranosyl iodide (105 mg), 14-O-tert-butyldimethylsilyladriamycinone (148 mg), mercuric bromide (183 mg), yellow-colored mercuric oxide (494 mg) and powder of Molecular Sieves 3A (720 mg) were suspended in anhydrous 1,2-dichloroethane (5 ml), and the resulting mixture was stirred at room temperature for 20 hrs. to effect the condensation reaction.

The resulting reaction solution was diluted with chloroform, filtered with aid of Celite to afford the filtrate. The residue from the filtration was washed with chloroform. The above filtrate was combined with the washings, and the resulting mixture was washed successively with a 30% aqueous potassium iodide solution, a saturated sodium hydrogen carbonate solution and water. The solution so washed with water was dried over anhydrous sodium sulfate and concentrated under a reduced pressure. The residue thus obtained was subjected to a silica gel column chromatography (developer: toluene-acetone, 12:1) to separate and purify the desired compound. The titled Compound (17) was obtained as a red solid (107 mg, yield 52%).

$^1$H-NMR spectrum (in deutero-chloroform): δ 5.74 (1H, d, H-1') 4.10 (3H, s, OCH$_3$) 2.14, 1.98 (each 3H, s, OAc)

(2) Preparation of 7-O-(2,6-dideoxy-2,6,6,6-tetrafluoro-α-L-talopyranosyl)adriamycinone [Compound (b) according to this invention]

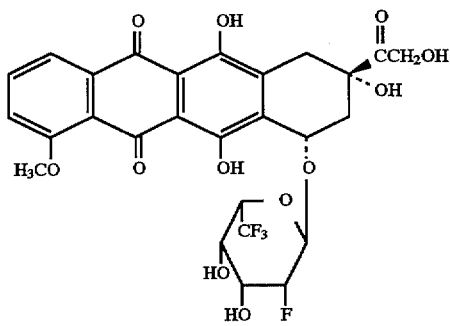

Compound (17) as obtained in the item (1) above, i.e. 7-O-(3,4-di-O-acetyl-2,6-dideoxy-2,6,6,6-tetrafluoro-α-L-talopyranosyl)-14-O-tert-butyldimethylsilyladriamycinone (98 mg) was suspended in anhydrous methanol (10 ml) and a 0.25N methanolic solution (0.3 ml) of sodium methoxide was added to the resulting suspension. The mixture obtained was stirred at room temperature for 3 hrs. to effect the elimination of the acetyl group from Compound (17). The resulting reaction solution, after addition of a small piece of dry ice thereto, was concentrated under a reduced pressure. The residue was diluted with chloroform, washed with water, dried over anhydrous sodium sulfate and concentrated under a reduced pressure. The resulting residue was dissolved in a mixture of chloroform-methanol and the solution obtained was subjected to a reprecipitation with addition of hexane, to yield the deacetylated product (67 mg) as a red solid.

The solid thus obtained was then dissolved in an 80% aqueous acetic acid solution (3 ml) and the solution was allowed to stand at 80° C. for 30 minutes (for elimination of TBS). The resulting reaction solution was concentrated under a reduced pressure and the residue was washed with water, dried under a reduced pressure, washed with toluene and then dried under a reduced pressure. The titled compound was obtained as a red solid (48 mg, yield 64%). This compound coincided with the final product as obtained in Example 2 in respect of the physical properties and spectra data.

Example 4

(1) Preparation of 7-O-(3,4-di-O-acetyl-2,6-dideoxy-6,6,6-trifluoro-α-L-lyxo-hexopyranosyl)-14-O-tert-butyldimethylsilyladriamycinone (Compound 18)

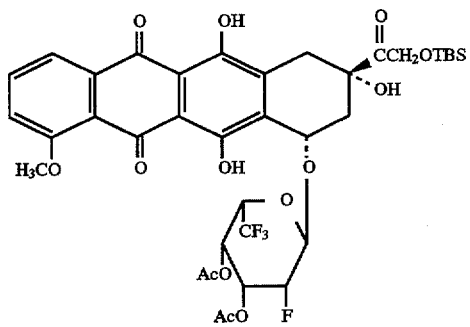

Compound (14) as obtained in Referential Example 2 (12), i.e. 3,4-di-O-acetyl-2,6-dideoxy-6,6,6-trifluoro-α-L-lyxo-hexopyranosyl bromide (85 mg), 14-O-tert-butyldimethylsilyladriamycinone [see D. Horton, W. Priebe and O. Varela, "The Journal of Antibiotics" Vol. 37, pp. 853–858 (1984)] (142 mg), mercuric bromide (174 mg), yellow-colored mercuric oxide (498 mg) and powder of Molecular Sieves 3A (696 mg) were suspended in anhydrous 1,2-dichloroethane (4 ml), and the resulting mixture was stirred at room temperature for 18 hrs. to conduct the condensation reaction.

The resulting reaction solution was diluted with chloroform, filtered with aid of Celite to give the filtrate. The residue from the filtration was washed with chloroform. The above filtrate and the washings were combined and the mixture was washed, successively, with a 30% aqueous potassium iodide solution, a saturated aqueous sodium hydrogen carbonate solution and water. The water-washed solution was dried over anhydrous sodium sulfate and concentrated under a reduced pressure. The residue so obtained was subjected twice to a silica gel column chromatography (The first developer: toluene-acetone, 10:1, and the second developer: chloroform-acetone, 30:1) to separate and purify the desired compound. The titled Compound (18) (50 mg, yield 26%) and β-anomer thereof (49 mg, yield 25%) were obtained each as a red solid.

[α]$_D^{19}$+195° (c 0.1, chloroform)

$^1$H-NMR spectrum (in deutero-chloroform): δ 5.73 (1H, br d, H-1') 4.09 (3H, s, OCH$_3$) 2.16, 1.95 (each 3H, s, OAc)

$^{19}$F-NMR spectrum (in deutero-chloroform, CFCl$_3$ as internal standard): δ −74.6 (d)

(2) Preparation of 7-O-(2,6-dideoxy-6,6,6-trifluoro-α-L-lyxo-hexopyranosyl)adriamycinone [Compound (c) according to this invention]

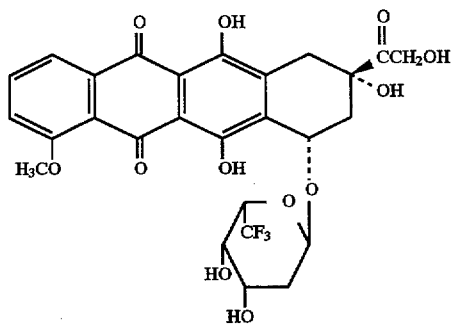

Compound (18) as obtained in the item (1) above, i.e. 7-O-(3,4-di-O-acetyl-2,6-dideoxy-6,6,6-trifluoro-α-L-lyxo-hexopyranosyl)-14-O-tert-butyldimethylsilyladriamycinone (40 mg) was suspended in anhydrous methanol (4 ml), and to the resulting suspension was added a 0.25N methanolic solution of sodium methoxide (0.13 ml). The mixture obtained was stirred at room temperature for 2.5 hrs. to effect the elimination of the acetyl group from Compound (18).

The resulting reaction solution, after a small piece of dry ice was added thereto, was concentrated under a reduced pressure. The residue obtained was diluted with chloroform, washed with water, dried over anhydrous sodium sulfate and then concentrated under a reduced pressure. The residue obtained was dissolved in a mixture of chloroform-methanol, and hexane was added to the solution to cause reprecipitation, so that the deacetylation product (27 mg) was obtained as a red solid.

This solid was then dissolved in an 80% aqueous acetic acid solution (1 ml), and the solution was allowed to stand at 80° C. for 30 minutes (for the elimination of TBS). The reaction solution obtained was concentrated under a reduced pressure, and the residue was washed with water, dried under a reduced pressure, washed with toluene and dried under a reduced pressure. Thus, there was afforded the titled compound, i.e. Compound (c) of this invention (21 mg, yield 69%) as a dark red solid.

[α]$_D^{21}$+188° (c 0.02, pyridine)

$^1$H-NMR spectrum (in deutero-pyridine): δ 5.95 (1H, br d, H-1') 3.98 (3H, s, OCH$_3$)

$^{19}$F-NMR spectrum (in deutero-pyridine, CFCl$_3$ as internal standard): δ −72.3 (d)

INDUSTRIAL UTILIZABILITY

Anthracycline derivatives of the general formula (I) and adriamycinone derivative of the formula (II) obtained according to this invention are characterized by that they contain a trifluoromethylated sugar and have very excellent anticancer or antitumor activities. The novel compounds of this invention are expected to be useful as anticancer or antitumor agents similarly to adriamycin.

We claim:
1. A daunomycinone or adriamycinone derivative represented by the following general formula:

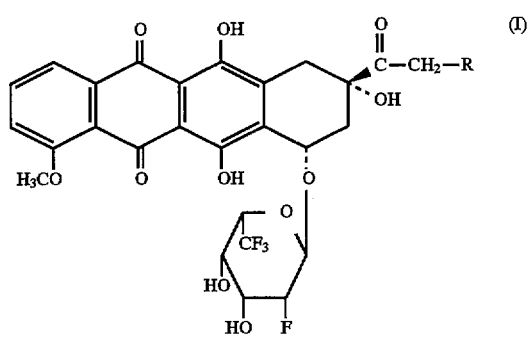

wherein R is a hydrogen atom or a hydroxyl group.

2. A derivative according to claim 1, which is 7-O-(2,6-dideoxy-2,6,6,6-tetrafluoro-α-L-talopyranosyl)daunomycinone represented by the following formula:

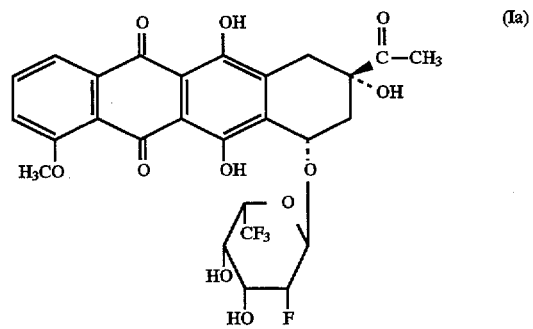

3. A derivative according to claim 1, which is 7-O-(2,6-dideoxy-2,6,6,6-tetrafluoro-α-L-talopyranosyl)adriamycinone represented by the following formula:

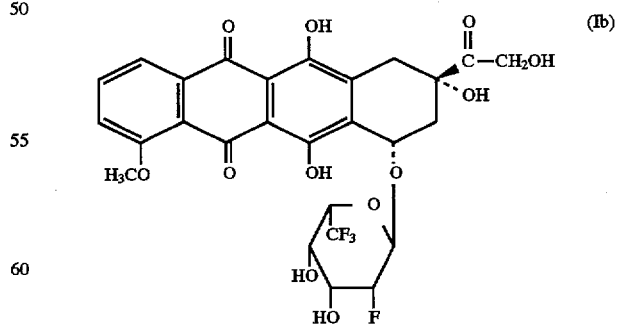

4. 7-O-(2,6-dideoxy-6,6,6-trifluoro-α-L-lyxo-hexopyranosyl)adriamycinone which is an adriamycinone derivative represented by the following formula:

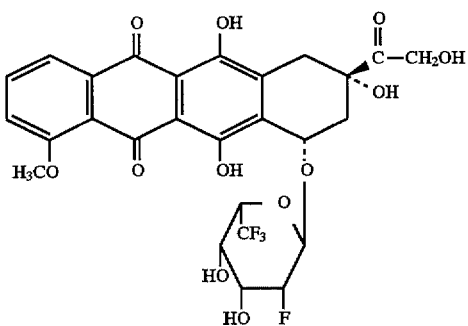

(II)

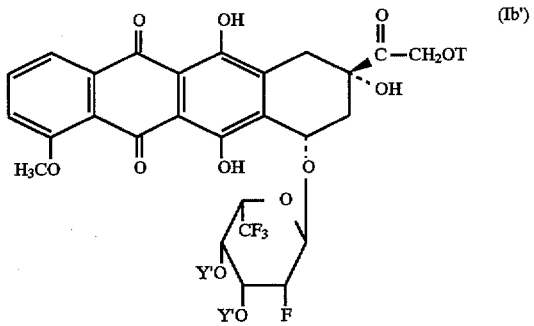

(Ib')

5. An antitumor composition comprising as an active ingredient a daunomycinone or adriamycinone derivative represented by the formula (II) described in claim 4, in combination with a pharmaceutically acceptable carrier.

6. An antitumor composition comprising as an active ingredient a daunomycinone or adriamycinone derivative represented by the general formula (I) described in claim 1, in combination with a pharmaceutically acceptable carrier.

7. A process for the preparation of 7-O-(2,6-dideoxy-2,6,6,6-tetrafluoro-α-L-talopyranosyl)adriamycinone represented by the following formula:

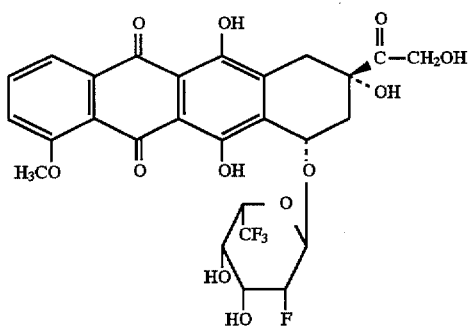

(Ib)

which comprises the steps of reacting a 14-O-protected adriamycinone represented by the following formula:

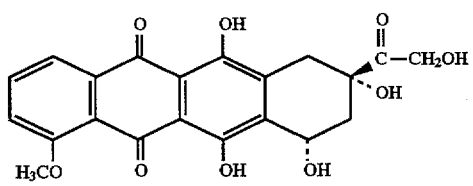

(C)

wherein T means a hydroxyl-protecting group, with a 3,4-di-O-protected 2,6-dideoxy-2,6,6,6-tetrafluoro-L-talopyranosyl halide represented by the following formula:

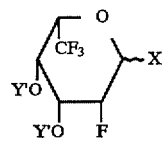

(IV)

wherein the two Y' are simultaneously acetyl groups or benzoyl groups as a hydroxyl-protecting group and X is an iodine or bromine atom, in an organic solvent and in the presence of a condensation catalyst, to produce a 14-O-protected 7-O-(3,4-di-O-protected-2,6-dideoxy-2,6,6,6-tetrafluoro-α-L-talopyranosyl)adriamycinone represented by the following formula:

wherein T and Y' have the same meanings as defined above; and then eliminating the groups T and Y' as the hydroxyl-protecting groups remaining in the resulting condensation product of the formula (Ib') therefrom.

8. A process for the preparation of 7-O-(2,6-dideoxy-6,6,6-trifluoro-α-L-lyxo-hexopyranosyl)adriamycinone represented by the following formula:

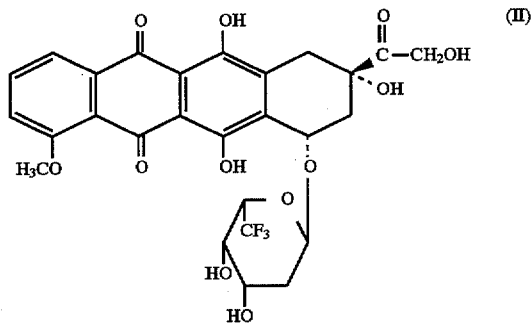

(II)

which comprises the steps of reacting a 14-O-protected adriamycinone represented by the following formula:

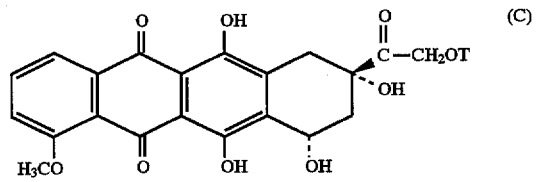

(C)

wherein T means a hydroxyl-protecting group, with a 3,4-di-O-protected-2,6-dideoxy-6,6,6-trifluoro-α-L-lyxo-hexopyranosyl halide represented by the following formula:

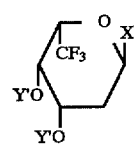

(XI)

wherein the two Y' groups are simultaneously acetyl groups or benzoyl groups as a hydroxyl-protecting group and X is an iodine or bromine atom, in an organic solvent and in the presence of a condensation catalyst, to produce a 14-O-protected 7-O-(3,4-di-O-protected-2,6-dideoxy-6,6,6-trifluoro-α-L-lyxo-hexopyranosyl)adriamycinone represented by the following formula:

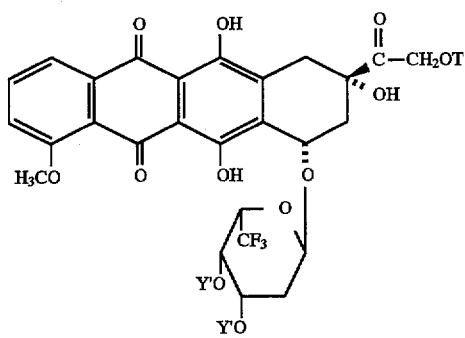

(II')

wherein T and Y' have the same meanings as defined above, and then eliminating the groups T and Y' as the hydroxyl-protecting groups remaining in the resulting condensation product of the formula (II') therefrom.

9. A process for the manufacture of a pharmaceutical composition comprising mixing 7-O-(2,6-dideoxy-2-6,6,6-tetrafluoro-α-L-talopyranosyl)adriamycinone of the formula (Ib) claimed in claim 3 with a pharmaceutically acceptable solid or liquid carrier.

10. A process for the manufacture of a pharmaceutical composition comprising mixing 7-O-(2,6-dideoxy-6,6,6-trifluoro-α-L-lyxo-hexopyranosyl)adriamycinone of the formula (II) claimed in claim 4, with a pharmaceutically acceptable solid or liquid carrier.

* * * * *

UNITED STATES PATENT AND TRADEMARK OFFICE
CERTIFICATE OF CORRECTION

PATENT NO. : 5,719,130
DATED : February 17, 1998
INVENTOR(S) : ANTHRACYCLINE DERIVATIVE HAVING A TRIFLUOROMETHYLATED SUGAR It is certified that error appears in the above-indentified patent and that said Letters Patent is hereby corrected as shown below:

Column 47, claim 4, formula (II) should read as follows:

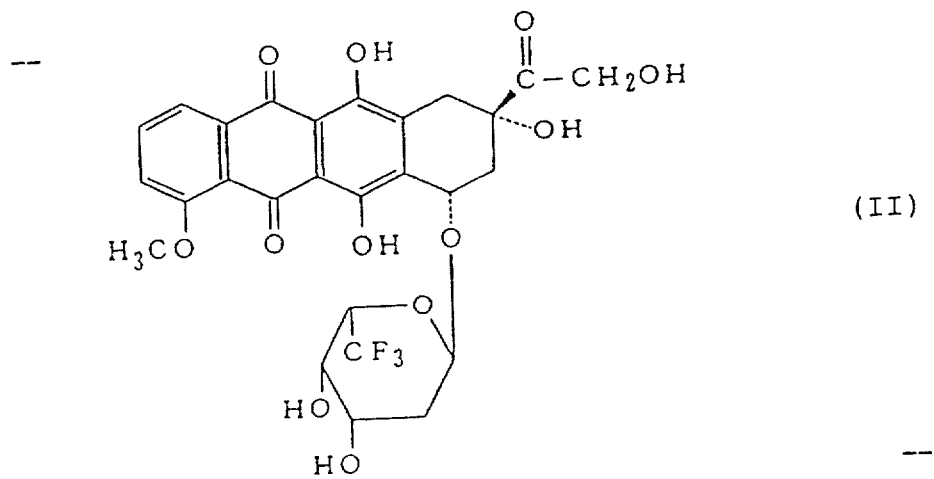

(II)

Signed and Sealed this

Fourth Day of May, 1999

Attest:

Attesting Officer

Q. TODD DICKINSON

Acting Commissioner of Patents and Trademarks